US008795673B2

(12) United States Patent
Li et al.

(10) Patent No.: US 8,795,673 B2
(45) Date of Patent: Aug. 5, 2014

(54) PREPARATION OF MAYTANSINOID ANTIBODY CONJUGATES BY A ONE-STEP PROCESS

(75) Inventors: Xinfang Li, Chestnut Hill, MA (US); Jared M. Worful, Somerville, MA (US)

(73) Assignee: ImmunoGen, Inc., Waltham, MA (US)

( * ) Notice: Subject to any disclaimer, the term of this patent is extended or adjusted under 35 U.S.C. 154(b) by 0 days.

(21) Appl. No.: 13/434,451

(22) Filed: Mar. 29, 2012

(65) Prior Publication Data

US 2012/0253021 A1 Oct. 4, 2012

Related U.S. Application Data

(60) Provisional application No. 61/468,997, filed on Mar. 29, 2011.

(51) Int. Cl.
*A61K 47/48* (2006.01)
*A61K 39/395* (2006.01)

(52) U.S. Cl.
USPC ..................... 424/178.1; 424/133.1

(58) Field of Classification Search
None
See application file for complete search history.

(56) References Cited

U.S. PATENT DOCUMENTS

| 4,137,230 A * | 1/1979 | Hashimoto et al. ........... 540/462 |
| 4,149,003 A | 4/1979 | Carlsson et al. |
| 4,256,746 A | 3/1981 | Miyashita et al. |
| 4,294,757 A | 10/1981 | Asai |
| 4,307,016 A | 12/1981 | Asai et al. |
| 4,313,946 A | 2/1982 | Powell et al. |
| 4,315,929 A | 2/1982 | Freedman et al. |
| 4,322,348 A | 3/1982 | Asai et al. |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,563,304 A | 1/1986 | Carlsson et al. |
| 4,664,911 A | 5/1987 | Uhr et al. |
| 4,780,210 A | 10/1988 | Hsia |
| 4,859,449 A | 8/1989 | Mattes |
| 5,024,834 A | 6/1991 | Houston et al. |
| 5,208,020 A * | 5/1993 | Chari et al. ................. 424/181.1 |
| 5,225,539 A | 7/1993 | Winter |
| 5,241,078 A | 8/1993 | Moreland et al. |
| 5,416,064 A | 5/1995 | Chari et al. |
| 5,475,092 A | 12/1995 | Chari et al. |
| 5,545,806 A | 8/1996 | Lonberg et al. |
| 5,552,293 A | 9/1996 | Lindholm et al. |
| 5,556,623 A * | 9/1996 | Barton et al. ................ 424/179.1 |
| 5,569,825 A | 10/1996 | Lonberg et al. |
| 5,580,853 A | 12/1996 | Sytkowski |
| 5,585,089 A | 12/1996 | Queen et al. |
| 5,585,499 A | 12/1996 | Chari et al. |
| 5,612,474 A | 3/1997 | Patel |
| 5,639,641 A | 6/1997 | Pedersen et al. |
| 5,665,357 A | 9/1997 | Rose et al. |
| 5,693,761 A | 12/1997 | Queen et al. |
| 5,693,762 A | 12/1997 | Queen et al. |
| 5,714,149 A | 2/1998 | Rhind et al. |
| 5,714,352 A | 2/1998 | Jakobovits |
| 5,747,446 A | 5/1998 | Sytkowski |
| 5,846,545 A | 12/1998 | Chari et al. |
| 5,885,793 A | 3/1999 | Griffiths et al. |
| 5,919,758 A | 7/1999 | Sytkowski |
| 5,965,714 A | 10/1999 | Ryall |
| 5,969,108 A | 10/1999 | McCafferty et al. |
| 6,171,586 B1 | 1/2001 | Lam et al. |
| 6,265,150 B1 | 7/2001 | Terstappen et al. |
| 6,316,003 B1 | 11/2001 | Frankel et al. |
| 6,333,410 B1 | 12/2001 | Chari et al. |
| 6,340,461 B1 | 1/2002 | Terman |
| 6,340,701 B1 | 1/2002 | Chari et al. |
| 6,372,738 B2 | 4/2002 | Chari et al. |

(Continued)

FOREIGN PATENT DOCUMENTS

| CA | 2006408 A1 | 6/1990 |
| EP | 0 239 400 A2 | 9/1987 |

(Continued)

OTHER PUBLICATIONS

Brinkman, Ulrich et al, PNAS, vol. 90, pp. 7538-7542, Aug. 1993, A recombinant immunotoxin containing a disulfide-stabilzied Fv fragment.*
Pastan, Ira et al, Cancer Research, vol. 51, pp. 3781-3787, 1991, Characterization of Monoclonal antibodies B1 and B3 that react with Mucinous Adenocarcinomas.*
Al-Katib, Ayad M. et al, Superior Antitumor Activity of SAR3419 to Rituximab in Xenograpt models for Non-Hodgkin's Lymphoma, vol. 15, pp. 4038-4045, 2009.*
Jensen, Markus et al, Cancer Letters, Mini-Review, Targeting the neural cell adhesion molecule in cancer, vol. 258, 2007, pp. 9-21.*
Yan, Li-Mei et al, Enhancement of the adhesive and spreading potentials of ovarian carcinoma RMG-1 cells due to increased expression of integrin a5b1 with the Lewis Y-structure on transfection of the alpha1,2-fucosyltransferase gene, Biochemie, vol. 92, 2010, pp. 852-857.*

(Continued)

*Primary Examiner* — Albert Navarro
*Assistant Examiner* — Ginny Portner
(74) *Attorney, Agent, or Firm* — Leydig, Voit & Mayer, Ltd.

(57) ABSTRACT

The invention provides a one-step process for preparing a cell-binding agent cytotoxic agent conjugate comprising contacting a cell-binding agent with a cytotoxic agent to form a first mixture comprising the cell-binding agent and the cytotoxic agent and contacting the first mixture comprising the cell-binding agent and the cytotoxic agent with a bifunctional crosslinking reagent, which provides a linker, in a solution having a pH of about 4 to about 9 to provide a second mixture comprising the cell-binding agent cytotoxic agent conjugate, wherein the cell-binding agent is chemically coupled through the linker to the cytotoxic agent, free cytotoxic agent, and reaction by-products. The second mixture is then optionally subjected to purification to provide a purified cell-binding agent cytotoxic agent conjugate.

25 Claims, No Drawings

(56) References Cited

U.S. PATENT DOCUMENTS

| | | | |
|---|---|---|---|
| 6,436,931 B1 | 8/2002 | Chari et al. | |
| 6,441,163 B1 * | 8/2002 | Chari et al. | 540/458 |
| 6,534,660 B1 | 3/2003 | Yongxin et al. | |
| 6,586,618 B1 | 7/2003 | Zhao et al. | |
| 6,596,757 B1 | 7/2003 | Chari et al. | |
| 6,630,579 B2 | 10/2003 | Chari et al. | |
| 6,632,979 B2 | 10/2003 | Erickson et al. | |
| 6,706,708 B2 | 3/2004 | Chari et al. | |
| 6,716,821 B2 | 4/2004 | Zhao et al. | |
| 6,756,397 B2 | 6/2004 | Zhao et al. | |
| 7,045,605 B2 | 5/2006 | Bander et al. | |
| 7,368,565 B2 | 5/2008 | Chari et al. | |
| 7,642,044 B2 * | 1/2010 | Thogersen et al. | 435/69.1 |
| 7,811,572 B2 * | 10/2010 | Dai et al. | 424/178.1 |
| 8,088,387 B2 * | 1/2012 | Steeves et al. | 424/181.1 |
| 8,383,122 B2 * | 2/2013 | Dai et al. | 424/178.1 |
| 8,557,966 B2 | 10/2013 | Ab et al. | |
| 8,624,003 B2 | 1/2014 | Kellogg et al. | |
| 2002/0150585 A1 * | 10/2002 | Marciani | 424/184.1 |
| 2002/0197266 A1 | 12/2002 | Debinski | |
| 2003/0004210 A1 | 1/2003 | Chari et al. | |
| 2003/0195365 A1 | 10/2003 | Zhao et al. | |
| 2004/0024049 A1 | 2/2004 | Baloglu et al. | |
| 2004/0192900 A1 | 9/2004 | Kunz et al. | |
| 2004/0220142 A1 * | 11/2004 | Marciani | 514/54 |
| 2004/0235840 A1 | 11/2004 | Chari et al. | |
| 2004/0241174 A1 | 12/2004 | Amphlett et al. | |
| 2005/0053608 A1 | 3/2005 | Weber et al. | |
| 2005/0112130 A1 * | 5/2005 | Bhat et al. | 424/155.1 |
| 2005/0118183 A1 | 6/2005 | Hoffee et al. | |
| 2005/0169933 A1 | 8/2005 | Steeves et al. | |
| 2005/0175619 A1 | 8/2005 | Duffy et al. | |
| 2005/0261232 A1 | 11/2005 | Strong et al. | |
| 2006/0073528 A1 * | 4/2006 | Lecerf et al. | 435/7.23 |
| 2006/0153834 A1 | 7/2006 | Carbonell et al. | |
| 2006/0182740 A1 | 8/2006 | Yang et al. | |
| 2006/0182750 A1 * | 8/2006 | Chari et al. | 424/155.1 |
| 2006/0193865 A1 | 8/2006 | Govindan | |
| 2006/0233811 A1 | 10/2006 | Chari | |
| 2007/0031402 A1 * | 2/2007 | Zhang et al. | 424/130.1 |
| 2007/0048314 A1 * | 3/2007 | Dai et al. | 424/145.1 |
| 2007/0154901 A1 * | 7/2007 | Thogersen et al. | 435/6 |
| 2007/0264257 A1 | 11/2007 | Dunussi-Joannopoulos et al. | |
| 2008/0166363 A1 * | 7/2008 | Govindan et al. | 424/178.1 |
| 2009/0274713 A1 * | 11/2009 | Chari et al. | 424/181.1 |
| 2010/0003719 A1 * | 1/2010 | Thagersen et al. | 435/69.1 |
| 2011/0064754 A1 | 3/2011 | Taylor et al. | |
| 2011/0166319 A1 * | 7/2011 | Dai et al. | 530/303 |
| 2011/0206658 A1 | 8/2011 | Crowley et al. | |
| 2012/0282175 A1 | 11/2012 | Carrigan et al. | |

FOREIGN PATENT DOCUMENTS

| | | | |
|---|---|---|---|
| EP | 0 425 235 A2 | 5/1991 | |
| EP | 1 258 255 A1 | 11/2001 | |
| EP | 2 468 304 A2 | 6/2012 | |
| GB | 2 188 638 A | 10/1987 | |
| WO | WO 92/01047 A1 | 1/1992 | |
| WO | WO 99/06587 A2 | 2/1999 | |
| WO | WO 00/02587 A1 | 1/2000 | |
| WO | 00/66091 * | 11/2000 | A61K 9/51 |
| WO | WO 01/24763 A2 | 4/2001 | |
| WO | WO 02/16368 A1 | 2/2002 | |
| WO | WO 02/16401 A2 | 2/2002 | |
| WO | WO 02/060955 A2 | 8/2002 | |
| WO | WO 02/092127 A1 | 11/2002 | |
| WO | WO 02/094325 A2 | 11/2002 | |
| WO | WO 02/098897 A2 | 12/2002 | |
| WO | WO 03/053462 A2 | 7/2003 | |
| WO | WO 03/057163 A2 | 7/2003 | |
| WO | WO 03/102132 A2 | 12/2003 | |
| WO | WO 2004/103272 A2 | 12/2004 | |
| WO | WO 2005/037992 A2 | 4/2005 | |
| WO | WO 2005/077090 A2 | 8/2005 | |
| WO | WO 2005/094882 A | 10/2005 | |
| WO | WO 2005/117986 A2 | 12/2005 | |
| WO | WO 2006/113623 A2 | 10/2006 | |
| WO | WO 2007/024536 A2 | 3/2007 | |
| WO | WO 2011/106528 A1 | 9/2011 | |
| WO | 2012112687 * | 8/2012 | A61K 47/48 |
| WO | 2012112708 * | 8/2012 | A61K 47/48 |

OTHER PUBLICATIONS

Baldus, SE et al, Histology and Histopathology, (2006), vol. 21, pp. 503-510, LewisY antigen (CD174) and apoptosis in gstric and colorectal carcinomas: correlations with clinical and prognostic parameters.*
Bergelt, Sabine et al, Listeriolysin O as cytotoxic component of an immunotoxin, Protein Science, 2009, vol. 18, pp. 1210-1220.*
Gao, Jian e tal, Journal of Experimental and Clinical Cancer Research, 2013, vol. 32(36) pp. 1-7, Expression of Lewis Y antigen and integrin av B3 in ovarian cancer and their relationship with chemotherapeutic drug resistance.*
International Search Report and Written Opinion issued in PCT Application No. PCT/US2012/31253, dated Dec. 7, 2012.
International Search Report and Written Opinion issued in PCT Application No. PCT/US2012/031243, dated Dec. 10, 2012.
Bhuyan et al., *Cancer Research*, 42(9): 3532-3537 (1982).
Boger et al., *Bioorg. Med. Chem. Lett.*, 1: 115-120 (1991).
Boger et al., *J. Org. Chem.*, 55: 5823-5833 (1990).
Boschetti et al., *Trends in Biotechnology*, 20(8): 333-337 (2002).
Burgess, *Immunology Today*, 5(6): 155-158 (1984).
Carlsson et al., *Biochem. J.*, 173: 723-737 (1978).
Chari et al., *Cancer Research*, 55(18): 4079-4084 (1995).
Chari et al., *Cancer Research*, 52(1): 127-131 (1992).
Christy et al., *Desalination*, 144(1-3): 133-136 (2002).
Colomer et al, *Cancer Invest.*, 19(1): 49-56 (2001).
Desmyter et al., *Nature Struct. Biol.*, 3(9): 803-811 (1996).
Erickson et al., *Cancer Research*, 66: 4426-4433 (2006).
Ghetie et al., *J. Immunological Methods*, 111(2): 267-277 (1988).
Greenberg et al., *Nature*, 374: 168-173 (1995).
Griffin et al., *Leukemia Res.*, 8(4): 521-534 (1984).
Haskard et al., *J. Immunological Methods*, 74(2): 361-367 (1984).
Heider et al., *Eur. J. Cancer*, 31A(13/14): 2385-2391 (1995).
Huse et al., *Science*, 246: 1275-1281 (1989).
Kawai et al., *Chem. Pharm. Bull.*, 32(9): 3441-3451 (1984).
Kellogg et al., *2009 AACR Annual Meeting*, Abstract 5480 (2009).
Kohler et al., *Eur. J. Immunol.*, 6: 511-519 (1976).
Kupchan et al., *J. Med. Chem.*, 21(1): 31-37 (1978).
Ladino et al., *Int. J. Cancer*, 73: 859-864 (1997).
Lewis et al., *Bioconjugate Chem.*, 12: 320-324 (2001).
Liu et al., *Cancer Research*, 57(17): 3629-3634 (1997).
Liu et al., *Proc. Natl. Acad. Sci. USA*, 93: 8618-8623 (1996).
Liu et al., *1997 AACR Annual Meeting*, Abstract 190 (1997).
Maloney et al., *Blood*, 90(6): 2188-2195 (1997).
Nadler et al., *J. Immunol.*, 131: 244-250 (1983).
Nisonoff et al., *Arch. Biochem. Biophys.*, 89: 230-244 (1960).
O'Keefe et al., *J. Biol. Chem.*, 260(1): 932-937 (1985).
Okamoto et al., *JP J. Cancer Research*, 83(7): 761-768 (1992).
Parham, *J. Immunol.*, 131: 2895-2902 (1983).
Pedersen et al., *J. Mol. Biol.*, 235: 959-973 (1994).
Pietersz, *Bioconjugate Chem.*, 1(2): 89-94 (1990).
Reider et al., *The Alkaloids*, XXIII: 71-73 (1984).
Reiter et al., *Protein Engineering*, 7: 697-704 (1994).
Ritz et al., *Nature*, 283: 583-585 (1980).
Roder et al., *Methods Enzymol*, 121: 140-167 (1986).
Roguska et al., *Proc. Natl. Acad. Sci. USA*, 91: 969-973 (1994).
Smith, *Current Opinion in Molecular Therapeutics*, 3(2): 198-203 (2001).
Spring et al., *J. Immunol.*, 113: 470-478 (1974).
Stanfield et al., *Science*, 305: 1770-1773 (2004).
Sytkowski et al., *Proc. Natl. Acad. Sci. USA*, 95: 1184-1188 (1998).
Taylor-Papadimitriou et al., *Int. J. Cancer*, 25: 17-21 (1981).
Trouet et al., *Proc. Natl. Acad. Sci. USA*, 79: 626-629 (1982).
Umemoto et al., *Int. J. Cancer*, 43(4): 677-684 (1989).
Van Hof et al., *Cancer Research*, 56(22): 5179-5185 (1996).
Warpehoski et al., *J. Med. Chem.*, 31: 590-603 (1988).

(56) References Cited

OTHER PUBLICATIONS

Welt et al., *J. Clin. Oncol.*, 12(6): 1193-1203 (1994).
U.S. Appl. No. 09/867,598, filed May 31, 2001.
U.S. Appl. No. 10/161,651, filed Jun. 5, 2002.
U.S. Appl. No. 11/352,121, filed Feb. 10, 2006.
U.S. Appl. No. 11/503,781, filed Aug. 14, 2006.
U.S. Appl. No. 12/793,175, filed Jun. 3, 2010.
U.S. Appl. No. 12/901,039, filed Oct. 8, 2010.
U.S. Appl. No. 12/975,695, filed Dec. 22, 2010.
U.S. Appl. No. 13/434,586, filed Mar. 29, 2012.
U.S. Appl. No. 13/776,097, filed Feb. 25, 2013.
U.S. Appl. No. 14/095,579, filed Dec. 3, 2013.
Al-Arif et al., *J. Lipid Research*, 10: 344-345 (1969).
Berg et al., *Biochemistry*, $5^{th}$ Ed., p. 1-8, New York: WH Freeman (2002).
Instructions for SMCC and Sulfo-SMCC, *Thermo Scientific*, p. 1-4 (2007).
International Search Report and Written Opinion issued in PCT Application No. PCT/US10/37046, dated Jul. 30, 2010.
Ugwu et al., *Pharmaceutical Technology*, p. 86, 88, 90, 92, 94, 96, 98, 100, 102, 104, 106, 108, 100-113 (2004).

\* cited by examiner

SEQUENCE LISTING

<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: Heavy Chain CDR1

<400> SEQUENCE: 1

Gly Tyr Phe Met Asn

```
<210> SEQ ID NO 2
<211> LENGTH: 17
<212> TYPE: PRT
<213> ORGANISM: Artificial Sequence
<220> FEATURE:
<223> OTHER INFORMATION: Heavy Chain CDR2
<220> FEATURE:
<221> NAME/KEY: MISC_FEATURE
<222> LOCATION: (14)..(14)
<223> OTHER INFORMATION: Xaa is Lys, Gln, His, or Arg
<220> FEATURE:
<221> NAME/KEY: MISC_FEATURE
<222> LOCATION: (16)..(16)
<223> OTHER INFORMATION: Xaa is Gln, His, Asn, or Arg
<220> FEATURE:
<221> NAME/KEY: MISC_FEATURE
<222> LOCATION: (17)..(17)
<223> OTHER INFORMATION: Xaa is Gly, Glu, Thr, Ser, Ala, or Val

<400> SEQUENCE: 2

Arg Ile His Pro Tyr Asp Gly Asp Thr Phe Tyr Asn Gln Xaa Phe Xaa
1               5                   10                  15

Xaa

<210> SEQ ID NO 3
<211> LENGTH: 9
<212> TYPE: PRT
<213> ORGANISM: Artificial Sequence
<220> FEATURE:
<223> OTHER INFORMATION: Heavy Chain CDR3

<400> SEQUENCE: 3

Tyr Asp Gly Ser Arg Ala Met Asp Tyr
1               5

<210> SEQ ID NO 4
<211> LENGTH: 15
<212> TYPE: PRT
<213> ORGANISM: Artificial Sequence
<220> FEATURE:
<223> OTHER INFORMATION: Light Chain CDR1

<400> SEQUENCE: 4

Lys Ala Ser Gln Ser Val Ser Phe Ala Gly Thr Ser Leu Met His
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: Light Chain CDR2

<400> SEQUENCE: 5

Arg Ala Ser Asn Leu Glu Ala
1               5

<210> SEQ ID NO 6
<211> LENGTH: 9
<212> TYPE: PRT
<213> ORGANISM: Artificial Sequence
<220> FEATURE:
<223> OTHER INFORMATION: Light Chain CDR3

<400> SEQUENCE: 6

Gln Gln Ser Arg Glu Tyr Pro Tyr Thr
```

-continued

<210> SEQ ID NO 7
<211> LENGTH: 17
<212> TYPE: PRT
<213> ORGANISM: Artificial Sequence
<220> FEATURE:
<223> OTHER INFORMATION: Heavy Chain CDR2

<400> SEQUENCE: 7

Arg Ile His Pro Tyr Asp Gly Asp Thr Phe Tyr Asn Gln Lys Phe Gln
1               5                   10                  15

Gly

<210> SEQ ID NO 8
<211> LENGTH: 448
<212> TYPE: PRT
<213> ORGANISM: Artificial Sequence
<220> FEATURE:
<223> OTHER INFORMATION: Heavy Chain

<400> SEQUENCE: 8

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Gly Tyr
                20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
    50                  55                  60

Gln Gly Lys Ala Thr Leu Thr Val Asp Lys Ser Ser Asn Thr Ala His
65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala

```
                275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
                355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445

<210> SEQ ID NO 9
<211> LENGTH: 117
<212> TYPE: PRT
<213> ORGANISM: Artificial Sequence
<220> FEATURE:
<223> OTHER INFORMATION: Heavy Chain Variable Domain

<400> SEQUENCE: 9

Gln Val Gln Leu Val Gln Ser Gly Ala Glu Val Val Lys Pro Gly Ala
1               5                   10                  15
Ser Val Lys Ile Ser Lys Ala Ser Gly Tyr Thr Phe Thr Gly Tyr Phe
            20                  25                  30
Met Asn Trp Val Lys Gln Ser Pro Gly Gln Ser Leu Glu Trp Ile Gly
        35                  40                  45
Arg Ile His Pro Tyr Asp Gly Asp Thr Phe Tyr Asn Gln Lys Phe Gln
    50                  55                  60
Gly Lys Ala Thr Leu Thr Val Asp Lys Ser Ser Asn Thr Ala His Met
65                  70                  75                  80
Glu Leu Leu Ser Leu Thr Ser Glu Asp Phe Ala Val Tyr Tyr Cys Thr
                85                  90                  95
Arg Tyr Asp Gly Ser Arg Ala Met Asp Tyr Trp Gly Gln Gly Thr Thr
            100                 105                 110
Val Thr Val Ser Ser
        115

<210> SEQ ID NO 10
<211> LENGTH: 112
<212> TYPE: PRT
<213> ORGANISM: Artificial Sequence
<220> FEATURE:
<223> OTHER INFORMATION: Light Chain Variable Domain

<400> SEQUENCE: 10

Asp Ile Val Leu Thr Gln Ser Pro Leu Ser Leu Ala Val Ser Leu Gly
1               5                   10                  15
```

```
Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
        50                  55                  60

Arg Phe Ser Gly Ser Gly Ser Lys Thr Asp Phe Thr Leu Asn Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110

<210> SEQ ID NO 11
<211> LENGTH: 112
<212> TYPE: PRT
<213> ORGANISM: Artificial Sequence
<220> FEATURE:
<223> OTHER INFORMATION: Light Chain Variable Domain

<400> SEQUENCE: 11

Asp Ile Val Leu Thr Gln Ser Pro Leu Ser Leu Ala Val Ser Leu Gly
1               5                   10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
        50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Gly Thr Lys Leu Glu Ile Lys Arg
            100                 105                 110
```

US 8,795,673 B2

PREPARATION OF MAYTANSINOID ANTIBODY CONJUGATES BY A ONE-STEP PROCESS

CROSS-REFERENCE TO RELATED APPLICATIONS

This patent application claims the benefit of U.S. Provisional Patent Application No. 61/468,997, filed Mar. 29, 2011, which is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing identified as follows: One 9,250 Byte ASCII (Text) file named "710087SequenceListing.TXT," created on Jun. 13, 2012.

BACKGROUND OF THE INVENTION

Antibody-Drug-Conjugates (ADC's) which are useful for the treatment of cancer and other diseases are commonly composed of three distinct elements: a cell-binding agent; a linker; and a cytotoxic agent. The conventional method of conjugating a cell-binding agent, such as an antibody, to a cytotoxic agent, employs two distinct reaction steps with the antibody. In the first reaction step (the modification step), the antibody is reacted with a heterobifunctional linker to produce a linker-modified antibody. The modified antibody product is then optionally purified from the excess linker or hydrolyzed linker reagent. In the second reaction step (the conjugation step), the linker-modified antibody is reacted with the cytotoxic agent containing a reactive group, such as thiol, to generate the antibody-cytotoxic agent conjugate, which is again purified in an additional purification step.

The processes that have been previously described for manufacture of the antibody-cytotoxic agent conjugates are complex because they are encumbered with steps that are cumbersome to perform or produce immunoconjugates that are less pure or less stable than optimally desired. Thus, it would be desirable to modify or eliminate one or more manufacturing steps while improving the product quality, such as purity and/or stability.

In view of the foregoing, there is a need in the art to develop improved processes for preparing cell-binding agent-cytotoxic agent conjugates that are of substantially high purity and can be prepared avoiding cumbersome steps and by reducing time and cost to the user. The invention provides such a process. These and other advantages of the invention, as well as additional inventive features, will be apparent from the description of the invention provided herein.

BRIEF SUMMARY OF THE INVENTION

The invention provides a process for preparing a cell-binding agent cytotoxic agent conjugate comprising the step of contacting a cell-binding agent with a cytotoxic agent to form a first mixture comprising the cell-binding agent and the cytotoxic agent, and then contacting the first mixture comprising the cell-binding agent and the cytotoxic agent with a bifunctional crosslinking reagent comprising a linker, in a solution having a pH of about 4 to about 9 to provide a mixture comprising (i) the cell-binding agent cytotoxic agent conjugate, wherein the cell-binding agent is chemically coupled through the linker to the cytotoxic agent, (ii) free cytotoxic agent, and (iii) reaction by-products. The process can further comprise the step of purifying the mixture to provide a purified cell-binding agent cytotoxic agent conjugate.

The processes of the present invention provide cell-binding agent cytotoxic agent conjugate with high purity and/or stability. To achieve the high purity and/or stability of the conjugate, it is essential that the cytotoxic agent is contacted with the cell-binding agent first to form a mixture comprising the cell-binding agent and the cytotoxic agent before the mixture is contacted with a bifunctional crosslinking reagent.

The present invention also includes a cell-binding agent cytotoxic agent conjugate prepared according to the processes described herein.

DETAILED DESCRIPTION OF THE INVENTION

The invention provides a one-step process for preparing a cell-binding agent cytotoxic agent conjugate. The process comprises contacting a cell-binding agent (e.g., an antibody) with a cytotoxic agent to form a first mixture comprising the cell-binding agent and the cytotoxic agent, and then contacting the first mixture comprising the cell-binding agent and the cytotoxic agent with a bifunctional crosslinking reagent comprising a linker, in a solution having a pH of about 4 to about 9 to provide a second mixture comprising the cell-binding agent cytotoxic agent conjugate, free cytotoxic agent, and reaction by-products, wherein the cell-binding agent is chemically coupled through the linker to the cytotoxic agent. The second mixture is then subjected to purification to provide a purified cell-binding agent cytotoxic agent conjugate.

In one embodiment, the contacting is effected by providing the cell-binding agent, then contacting the cell-binding agent with the cytotoxic agent to form a first mixture comprising the cell-binding agent and the cytotoxic agent, and then contacting the first mixture comprising the cell-binding agent and the cytotoxic agent with the bifunctional crosslinking reagent. For example, in one embodiment, the cell-binding agent is provided in a reaction vessel, the cytotoxic agent is added to the reaction vessel (thereby contacting the cell-binding agent), and then the bifunctional crosslinking reagent is added to the mixture comprising the cell-binding agent and the cytotoxic agent (thereby contacting the mixture comprising the cell-binding agent and the cytotoxic agent). In one embodiment, the cell-binding agent is provided in a reaction vessel, and the cytotoxic agent is added to the reaction vessel immediately following providing the cell-binding agent to the vessel. In another embodiment, the cell-binding agent is provided in a reaction vessel, and the cytotoxic agent is added to the reaction vessel after a time interval following providing the cell-binding agent to the vessel (e.g., about 5 minutes, about 10 minutes, about 20 minutes, about 30 minutes, about 40 minutes, about 50 minutes, about 1 hour, about 1 day or longer after providing the cell-binding agent to the space). The cytotoxic agent can be added quickly (i.e., within a short time interval, such as about 5 minutes, about 10 minutes) or slowly (such as by using a pump).

The mixture comprising the cell-binding agent and the cytotoxic agent can be then contacted with the bifunctional crosslinking reagent either immediately after contacting the cell-binding agent with the cytotoxic agent or at some later point (e.g., about 5 minutes to about 8 hours or longer) after contacting the cell-binding agent with the cytotoxic agent. For example, in one embodiment, the bifunctional crosslinking reagent is added to the mixture comprising the cell-binding agent and the cytotoxic agent immediately after the addition of the cytotoxic agent to the reaction vessel comprising the cell-binding agent. Alternatively, the mixture comprising the cell-binding agent and the cytotoxic agent can be contacted with the bifunctional crosslinking reagent at about 5 minutes, about 10 minutes, about 20 minutes, about 30 minutes, about 1 hour, about 2 hours, about 3 hours, about 4 hours, about 5 hours, about 6 hours, about 7 hours, about 8 hours, or longer after contacting the cell-binding agent with the cytotoxic agent.

In another embodiment, the cytotoxic agent and the bifunctional agent are added through multiple cycles (e.g., 1, 2, 3, 4, 5 or more cycles). For example, the invention provides a process comprising the steps of: a) contacting a cell-binding agent with a cytotoxic agent to form a first mixture comprising the cell-binding agent and the cytotoxic agent; and then contacting the first mixture with a bifunctional crosslinking reagent comprising a linker, in a solution having a pH of about 4 to about 9 to provide a second mixture comprising the cell-binding agent cytotoxic agent conjugate, free cytotoxic agent, and reaction by-products, wherein the cell-binding agent is chemically coupled through the linker to the cytotoxic agent; b) contacting the second mixture with the cytotoxic agent to form a third mixture; and then contacting the third mixture with the bifunctional crosslinking reagent at a pH of about 4 to about 9 to provide a fourth mixture; and c) purifying the fourth mixture to provide the purified cell-binding agent cytotoxic agent conjugate. In one embodiment, step b) is carried out after a time interval (e.g., about 1 hour, about 2 hours, about 3 hours or longer) following step a). In another embodiment, step b) can be repeated several times (e.g., 1, 2, 3, 4 or more times) before step c) is carried out. The additional step b) can be carried out after a time interval (e.g., about 1 hour, about 2 hours, about 3 hours or longer) following the initial step b).

In another embodiment, the bifunctional crosslinking reagent is added before the complete addition of the cytotoxic agent. For example, in one embodiment, the cytotoxic agent is added to the cell-binding agent continuously over a time interval (e.g., over about 5 minutes, about 10 minutes, about 30 minutes, about 1 hour, about 2 hours, about 3 hours, or longer) to form a mixture comprising the cell-binding agent and the cytotoxic agent. Before the addition of the cytotoxic agent is complete, the bifunctional crosslinking reagent is added to the mixture comprising the cell-binding agent and the cytotoxic agent, provided that at any time, the cytotoxic agent is in molar excess of the bifunctional crosslinking reagent. In one embodiment, the bifunctional crosslinking reagent is added continuously over a time interval (e.g., over about 5 minutes, about 10 minutes, about 30 minutes, about 1 hour, about 2 hours, about 3 hours, or longer).

After the mixture comprising the cell-binding agent and the cytotoxic agent is contacted with the bifunctional crosslinking reagent, the reaction is allowed to proceed for about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or longer (e.g., about 30 hours, about 35 hours, about 40 hours, about 45 hours, or about 48 hrs).

Contacting the cell-binding agent with the cytotoxic agent and then the bifunctional crosslinking reagent (i.e., the reaction step) occurs in a solution having a pH of about 4 to about 9 (e.g., about 4, about 4.5, about 5, about 5.5, about 6, about 6.5, about 7, about 7.5, about 8, about 8.5, or about 9). In one embodiment, the reaction step occurs in a solution having a pH of about 6 or less (e.g., about 4 to about 6, about 4 to about 5.5, or about 4.5 to about 5.5).

In another embodiment, the inventive process comprises contacting a cell-binding agent with a cytotoxic agent and then a bifunctional crosslinking reagent in a solution having a pH of about 6 or greater (e.g., about 6 to about 9, about 6 to about 7, about 7 to about 9, about 7 to about 8.5, about 7.5 to about 8.5, about 7.5 to about 8.0, about 8.0 to about 9.0, or about 8.5 to about 9.0). For example, the inventive process comprises contacting a cell-binding agent with a cytotoxic agent and a bifunctional crosslinking reagent in a solution having a pH of about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, or about 9.0. In a specific embodiment, the inventive process comprises contacting a cell-binding agent with a cytotoxic agent and a bifunctional crosslinking reagent in a solution having a pH of about 7.8 (e.g., a pH of 7.6 to 8.0 or a pH of 7.7 to 7.9).

The inventive process comprises performing the one-step reaction (i.e., contacting a cell-binding agent with a cytotoxic agent and then a bifunctional crosslinking reagent) at any suitable temperature known in the art. For example, the one-step reaction can occur at about 20° C. or less (e.g., about −10° C. (provided that the solution is prevented from freezing, e.g., by the presence of organic solvent used to dissolve the cytotoxic agent and the bifunctional crosslinking reagent) to about 20° C., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, contacting a cell-binding agent with a cytotoxic agent and a bifunctional crosslinking reagent occurs at a temperature of about 16° C. to about 24° C. (e.g., about 16° C., about 17° C., about 18° C., about 19° C., about 20° C., about 21° C., about 22° C., about 23° C., about 24° C., or about 25° C.).

In another embodiment, contacting a cell-binding agent with a cytotoxic agent and then a bifunctional crosslinking reagent occurs at a temperature of about 15° C. or less (e.g., about −10° C. to about 15° C., or about 0° C. to about 15° C.). In this respect, the inventive process comprises contacting a cell-binding agent with a cytotoxic agent and then a bifunctional crosslinking reagent at a temperature of about 15° C., about 14° C., about 13° C., about 12° C., about 11° C., about 10° C., about 9° C., about 8° C., about 7° C., about 6° C., about 5° C., about 4° C., about 3° C., about 2° C., about 1° C., about 0° C., about −1° C., about −2° C., about −3° C., about −4° C., about −5° C., about −6° C., about −7° C., about −8° C., about −9° C., or about −10° C., provided that the solution is prevented from freezing, e.g., by the presence of organic solvent(s) used to dissolve the bifunctional crosslinking reagent. In one embodiment, the inventive process comprises contacting a cell-binding agent with a cytotoxic agent and then a bifunctional crosslinking reagent at a temperature of about −10° C. to about 15° C., about 0° C. to about 15° C., about 0° C. to about 10° C., about 0° C. to about 5° C., about 5° C. to about 15° C., about 10° C. to about 15° C., or about 5° C. to about 10° C. In another embodiment, the inventive process comprises contacting a cell-binding agent with a cytotoxic agent and then a bifunctional crosslinking reagent at a temperature of about 10° C. (e.g., a temperature of 8° C. to 12° C. or a temperature of 9° C. to 11° C.).

In one embodiment, the inventive process comprises contacting a cell-binding agent with a cytotoxic agent and then a bifunctional crosslinking reagent in a solution having a high pH (e.g., about 7 or greater) at a low temperature (e.g., about 15° C. or less). For example, in one embodiment, the inventive process comprises contacting a cell-binding agent with a cytotoxic agent and then a bifunctional crosslinking reagent in a solution having a pH of about 7.5 at a temperature of about 15° C., in a solution having a pH of about 7.8 at a temperature of about 10° C., in a solution having a pH about 8.2 at a temperature of about 0° C., or in a solution having a pH about 8.5 at a temperature of about 0° C. In another embodiment, the inventive process comprises contacting a cell-binding agent with a cytotoxic agent and then a bifunctional crosslinking reagent in a solution having a pH of 7.0 to 8.5 (e.g., a pH of 7.5 to 8.0) at a temperature of 5° C. to 15° C.

In one embodiment, the inventive process further comprises a quenching step to quench any unreacted cytotoxic agent and/or unreacted bifunctional crosslinking reagent. The quenching step is performed prior to purification of the cell-binding agent cytotoxic agent. For example, the inventive process comprises (a) contacting a cell-binding agent with a cytotoxic agent to form a mixture comprising the cell-binding agent and the cytotoxic agent and then contacting the mixture comprising the cell-binding agent and the cytotoxic agent with a bifunctional crosslinking reagent comprising a linker, in a solution having a pH of about 4 to about 9 to provide a mixture comprising (i) the cell-binding agent cytotoxic agent conjugate, wherein the cell-binding agent is chemically coupled through the linker to the cytotoxic agent, (ii) free cytotoxic agent, and (iii) reaction by-products, (b) quenching the mixture prepared in step (a) to quench any unreacted cytotoxic agent and/or unreacted bifunctional crosslinking reagent, and (c) purifying the mixture to provide a purified cell-binding agent cytotoxic agent conjugate.

In one embodiment, the mixture is quenched by contacting the mixture with a quenching reagent. As used herein, the "quenching reagent" refers to a reagent that reacts with the free cytotoxic agent and/or the bifunctional crosslinking reagent.

In one embodiment, maleimide or haloacetamide quenching reagents, such as 4-maleimidobutyric acid, 3-maleimidopropionic acid, N-ethylmaleimide, iodoacetamide, or iodoacetamidopropionic acid, can be used to ensure that any unreacted group (such as thiol) in the cytotoxic agent is quenched. The quenching step can help prevent the dimerization of the cytotoxic agent, particular the cytotoxic agent having an unreacted thiol group (such as DM1). The dimerized cytotoxic agent can be difficult to remove. The quenching step may also minimize any unwanted thiol-disulfide interchange reaction with the native antibody disulfide groups. Upon quenching with polar, charged thiol-quenching reagents (such as 4-maleimidobutyric acid or 3-maleimidopropionic acid), the excess, unreacted cytotoxic agent is converted into a polar, charged, water-soluble adduct that can be easily separated from the covalently-linked conjugate during the purification step. Quenching with non-polar and neutral thiol-quenching reagents can also be used.

In one embodiment, the mixture is quenched by contacting the mixture with a quenching reagent that reacts with the unreacted bifunctional crosslinking reagent. For example, nucleophiles can be added to the mixture in order to quench any unreacted bifunctional crosslinking reagent. The nucleophile preferably is an amino group containing nucleophile, such as lysine, taurine and hydroxylamine.

In a preferred embodiment, the reaction (i.e., contacting a cell-binding agent with a cytotoxic agent and then a bifunctional crosslinking reagent) is allowed to proceed to completion prior to contacting the mixture with a quenching reagent. In this regard, the quenching reagent is added to the mixture about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 25 hours to about 48 hours) after the mixture comprising the cell-binding agent and the cytotoxic agent is contacted with the bifunctional crosslinking reagent.

The inventive process may optionally include the addition of sucrose to the reaction step (i.e., contacting a cell-binding agent with a cytotoxic agent and a bifunctional crosslinking reagent) to increase solubility and recovery of the cell-binding agent-cytotoxic agent conjugates. Desirably, sucrose is added at a concentration of about 0.1% (w/v) to about 20% (w/v) (e.g., about 0.1% (w/v), 1% (w/v), 5% (w/v), 10% (w/v), 15% (w/v), or 20% (w/v)). Preferably, sucrose is added at a concentration of about 1% (w/v) to about 10% (w/v) (e.g., about 0.5% (w/v), about 1% (w/v), about 1.5% (w/v), about 2% (w/v), about 3% (w/v), about 4% (w/v), about 5% (w/v), about 6% (w/v), about 7% (w/v), about 8% (w/v), about 9% (w/v), about 10% (w/v), or about 11% (w/v)). In addition, the reaction step also can comprise the addition of a buffering agent. Any suitable buffering agent known in the art can be used. Suitable buffering agents include, for example, a citrate buffer, an acetate buffer, a succinate buffer, and a phosphate buffer. In one embodiment, the buffering agent is selected from the group consisting of HEPPSO(N-(2-hydroxyethyl)piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and a combination thereof.

Following the reaction step, the cell-binding agent cytotoxic agent conjugate is subjected to a purification step. In this regard, the cell-binding agent cytotoxic agent conjugate can be purified from the other components of the mixture (e.g., free cytotoxic agent and reaction by-products) using tangential flow filtration (TFF), which is a membrane-based tangential flow filtration process, non-adsorptive chromatography, adsorptive chromatography, adsorptive filtration, selective precipitation, or any other suitable purification process, as well as combinations thereof. In one embodiment of the invention, the cell-binding agent cytotoxic agent conjugate is purified using a single purification step (e.g., TFF). Preferably, the conjugate is purified and exchanged into the appropriate formulation using a single purification step (e.g., TFF). In another embodiment of the invention, the cell-binding agent cytotoxic agent conjugate is purified using two sequential purification steps. For example, the conjugate can be first purified by selective precipitation, adsorptive filtration, absorptive chromatography or non-absorptive chromatography, followed by purification with TFF. One of ordinary skill in the art will appreciate that purification of the cell-binding agent cytotoxic agent conjugate enables the isolation of a stable conjugate comprising the cell-binding agent chemically coupled to the cytotoxic agent.

Any suitable TFF systems may be utilized for purification, including a Pellicon type system (Millipore, Billerica, Mass.), a Sartocon Cassette system (Sartorius AG, Edgewood, N.Y.), and a Centrasette type system (Pall Corp., East Hills, N.Y.).

Any suitable adsorptive chromatography resin may be utilized for purification. Preferred adsorptive chromatography resins include hydroxyapatite chromatography, hydrophobic charge induction chromatography (HCIC), hydrophobic interaction chromatography (HIC), ion exchange chromatography, mixed mode ion exchange chromatography, immobilized metal affinity chromatography (IMAC), dye ligand chromatography, affinity chromatography, reversed phase chromatography, and combinations thereof. Examples of suitable hydroxyapatite resins include ceramic hydroxyapatite (CHT Type I and Type II, Bio-Rad Laboratories, Hercules, Calif.), HA Ultrogel hydroxyapatite (Pall Corp., East Hills, N.Y.), and ceramic fluoroapatite (CFT Type I and Type II, Bio-Rad Laboratories, Hercules, Calif.). An example of a suitable HCIC resin is MEP Hypercel resin (Pall Corp., East Hills, N.Y.). Examples of suitable HIC resins include Butyl-Sepharose, Hexyl-Sepaharose, Phenyl-Sepharose, and Octyl Sepharose resins (all from GE Healthcare, Piscataway, N.J.), as well as Macro-prep Methyl and Macro-Prep t-Butyl resins (Biorad Laboratories, Hercules, Calif.). Examples of suitable ion exchange resins include SP-Sepharose, CM-Sepharose, and Q-Sepharose resins (all from GE Healthcare, Piscataway, N.J.), and Unosphere S resin (Bio-Rad Laboratories, Hercules, Calif.). Examples of suitable mixed mode ion exchangers include Bakerbond ABx resin (JT Baker, Phillipsburg N.J.). Examples of suitable IMAC resins include Chelating Sepharose resin (GE Healthcare, Piscataway, N.J.) and Profinity IMAC resin (Bio-Rad Laboratories, Hercules, Calif.). Examples of suitable dye ligand resins include Blue Sepharose resin (GE Healthcare, Piscataway, N.J.) and Affi-gel Blue resin (Bio-Rad Laboratories, Hercules, Calif.). Examples of suitable affinity resins include Protein A Sepharose resin (e.g., MabSelect, GE Healthcare, Piscataway, N.J.), where the cell-binding agent is an antibody, and lectin affinity resins, e.g. Lentil Lectin Sepharose resin (GE Healthcare, Piscataway, N.J.), where the cell-binding agent bears appropriate lectin binding sites. Alternatively an antibody specific to the cell-binding agent may be used. Such an antibody can be immobilized to, for instance, Sepharose 4 Fast Flow resin (GE Healthcare, Piscataway, N.J.). Examples of suitable reversed phase resins include C4, C8, and C18 resins (Grace Vydac, Hesperia, Calif.).

Any suitable non-adsorptive chromatography resin may be utilized for purification. Examples of suitable non-adsorptive chromatography resins include, but are not limited to, SEPHADEX™ G-25, G-50, G-100, SEPHACRYL™ resins (e.g., S-200 and S-300), SUPERDEX™ resins (e.g., SUPERDEX™ 75 and SUPERDEX™ 200), BIO-GEL® resins (e.g., P-6, P-10, P-30, P-60, and P-100), and others known to those of ordinary skill in the art.

In one embodiment, the inventive process further comprises a holding step to release the unstably bound linkers from the cell-binding agent. The holding step comprises holding the mixture prior to purification of the cell-binding agent-cytotoxic agent conjugate (e.g., after the reaction step, between the reaction step and the quenching step, or after the quenching step). For example, the inventive process comprises (a) contacting a cell-binding agent with a cytotoxic agent to form a mixture comprising the cell-binding agent and the cytotoxic agent; and then contacting the mixture comprising the cell-binding agent and the cytotoxic agent with a bifunctional crosslinking reagent, which provides a linker, in a solution having a pH of about 4 to about 9 to provide a mixture comprising (i) the cell-binding agent cytotoxic agent conjugate, wherein the cell-binding agent is chemically coupled through the linker to the cytotoxic agent, (ii) free cytotoxic agent, and (iii) reaction by-products, (b) holding the mixture prepared in step (a) to release the unstably bound linkers from the cell-binding agent, and (c) purifying the mixture to provide a purified cell-binding agent cytotoxic agent conjugate.

In another embodiment, the inventive process comprises (a) contacting a cell-binding agent with a cytotoxic agent to form a mixture comprising the cell-binding agent and the cytotoxic agent; and then contacting the mixture comprising the cell-binding agent and the cytotoxic agent with a bifunctional crosslinking reagent, which provides a linker, in a solution having a pH of about 4 to about 9 to provide a mixture comprising (i) the cell-binding agent cytotoxic agent conjugate, wherein the cell-binding agent is chemically coupled through the linker to the cytotoxic agent, (ii) free cytotoxic agent, and (iii) reaction by-products, (b) quenching the mixture prepared in step (a) to quench any unreacted cytotoxic agent and/or unreacted bifunctional crosslinking reagent, (c) holding the mixture prepared in step (b) to release the unstably bound linkers from the cell-binding agent, and (d) purifying the mixture to provide a purified cell-binding agent cytotoxic agent conjugate.

Alternatively, the holding step can be performed after purification of the cell-binding agent-cytotoxic agent conjugate, followed by an additional purification step.

In a preferred embodiment, the reaction (i.e., contacting a cell-binding agent with a cytotoxic agent and then a bifunctional crosslinking reagent) is allowed to proceed to completion prior to the holding step. In this regard, the holding step can be performed about 1 hour to about 48 hours (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, or about 24 hours to about 48 hours) after the mixture comprising the cell-binding agent and the cytotoxic agent is contacted with the bifunctional crosslinking reagent.

The holding step comprises maintaining the solution at a suitable temperature (e.g., about 0° C. to about 37° C.) for a suitable period of time (e.g., about 1 hour to about 1 week, about 1 hour to about 24 hours, about 1 hour to about 8 hours, or about 1 hour to about 4 hours) to release the unstably bound linkers from the cell-binding agent while not substantially releasing the stably bound linkers from the cell-binding agent. In one embodiment, the holding step comprises maintaining the solution at about 20° C. or less (e.g., about 0° C. to about 18° C., about 4° C. to about 16° C.), at room temperature (e.g., about 20° C. to about 30° C. or about 20° C. to about 25° C.), or at an elevated temperature (e.g., about 30° C. to about 37° C.). In one embodiment, the holding step comprises maintaining the solution at a temperature of about 16° C. to about 24° C. (e.g., about 15° C., about 16° C., about 17° C., about 18° C., about 19° C., about 20° C., about 21° C., about 22° C., about 23° C., about 24° C., or about 25° C.). In another embodiment, the holding step comprises maintaining the solution at a temperature of about 2° C. to about 8° C. (e.g., about 0° C., about 1° C., about 2° C., about 3° C., about 4° C., about 5° C., about 6° C., about 7° C., about 8° C., about 9° C., or about 10° C.). In another embodiment, the holding step comprises maintaining the solution at a temperature of about 37° C. (e.g., about 34° C., about 35° C., about 36° C., about 37° C., about 38° C., about 39° C., or about 40° C.).

The duration of the holding step depends on the temperature and the pH at which the holding step is performed. For example, the duration of the holding step can be substantially reduced by performing the holding step at elevated temperature, with the maximum temperature limited by the stability of the cell-binding agent-cytotoxic agent conjugate. The holding step can comprise maintaining the solution for about 1 hour to about 1 day (e.g., about 1 hour, about 2 hours, about 3 hours, about 4 hours, about 5 hours, about 6 hours, about 7 hours, about 8 hours, about 9 hours, about 10 hours, about 12 hours, about 14 hours, about 16 hours, about 18 hours, about 20 hours, about 22 hours, or about 24 hours), about 10 hours to about 24 hours, about 12 hours to about 24 hours, about 14 hours to about 24 hours, about 16 hours to about 24 hours, about 18 hours to about 24 hours, about 20 hours to about 24 hours, about 5 hours to about 1 week, about 20 hours to about 1 week, about 12 hours to about 1 week (e.g., about 12 hours, about 16 hours, about 20 hours, about 24 hours, about 2 days, about 3 days, about 4 days, about 5 days, about 6 days, or about 7 days), or about 1 day to about 1 week.

In one embodiment, the holding step comprises maintaining the solution at a temperature of about 2° C. to about 8° C. for a period of at least about 12 hours for up to a week. In another embodiment, the holding step comprises maintaining the solution at a temperature of about 2° C. to about 8° C. overnight (e.g., about 12 to about 24 hours, preferably about 20 hours).

The pH value for the holding step preferably is about 4 to about 10. In one embodiment, the pH value for the holding step is about 4 or more, but less than about 6 (e.g., 4 to 5.9) or about 5 or more, but less than about 6 (e.g., 5 to 5.9). In another embodiment, the pH values for the holding step range from about 6 to about 10 (e.g., about 6.5 to about 9, about 6 to about 8). For example, pH values for the holding step can be about 6, about 6.5, about 7, about 7.5, about 8, about 8.5, about 9, about 9.5, or about 10.

In specific embodiments, the holding step can comprise incubating the mixture at 25° C. at a pH of about 6-7.5 for about 12 hours to about 1 week, incubating the mixture at 4° C. at a pH of about 4.5-5.9 for about 5 hours to about 5 days, or incubating the mixture at 25° C. at a pH of about 4.5-5.9 for about 5 hours to about 1 day.

The invention provides a process for preparing compositions of stable conjugates comprising a cell-binding agent chemically coupled to a cytotoxic agent, wherein the compositions are substantially free of unstable conjugates. In this respect, the invention provides a process for preparing cell-binding agent-cytotoxic agent conjugate of substantially high purity and stability. Such compositions can be used for treating diseases because of the high purity and stability of the conjugates. Compositions comprising a cell-binding agent, such as an antibody, chemically coupled to a cytotoxic agent, such as a maytansinoid, are described in, for example, U.S. Pat. No. 7,374,762, the entire teaching of which is incorporated herein by reference in its entirety. In one aspect of the invention, a cell-binding agent-cytotoxic agent conjugate of substantially high purity has one or more of the following features: (a) greater than about 90% (e.g., greater than or equal to about 91%, 92%, 93%, 94%, 95%, 96%, 97%, 98%, 99%, or 100%), preferably greater than about 95%, of conjugate species are monomeric, (b) unconjugated linker level in the conjugate preparation is less than about 10% (e.g., less than or equal to about 9%, 8%, 7%, 6%, 5%, 4%, 3%, 2%, 1%, or 0%) (relative to total linker), (c) less than 10% of conjugate species are crosslinked (e.g., less than or equal to about 9%, 8%, 7%, 6%, 5%, 4%, 3%, 2%, 1%, or 0%), (d) free cytotoxic agent level in the conjugate preparation is less than about 2% (e.g., less than or equal to about 1.5%, 1.4%, 1.3%, 1.2%, 1.1%, 1.0%, 0.9%, 0.8%, 0.7%, 0.6%, 0.5%, 0.4%, 0.3%, 0.2%, 0.1%, or 0%) (mol/mol relative to total cytotoxic agent) and/or (e) no substantial increase in the level of free cytotoxic agent upon storage (e.g., after about 1 week, about 2 weeks, about 3 weeks, about 1 month, about 2 months, about 3 months, about 4 months, about 5 months, about 6 months, about 1 year, about 2 years, about 3 years, about 4 years, or about 5 years). "Substantial increase" in the level of free cytotoxic agent means that after certain storage time (e.g., about 1 week, about 2 weeks, about 3 weeks, about 1 month, about 2 months, about 3 months, about 4 months, about 5 months, about 6 months, about 1 year, about 2 years, about 3 years, about 4 years, or about 5 years), the increase in the level of free cytotoxic agent is less than about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.2%, about 2.5%, about 2.7%, about 3.0%, about 3.2%, about 3.5%, about 3.7%, or about 4.0%.

As used herein, the term "unconjugated linker" refers to the cell-binding agent that is covalently linked with the bifunctional crosslinking reagent, wherein the cell-binding agent is not covalently coupled to the cytotoxic agent through the linker of the bifunctional crosslinking reagent (i.e., the "unconjugated linker" can be represented by CBA-L, wherein CBA represents the cell-binding agent and L represents the bifunctional crosslinking reagent. In contrast, the cell-binding agent cytotoxic agent conjugate can be represented by CBA-L-D, wherein D represents the cytotoxic agent).

In one embodiment, the average molar ratio of the cytotoxic agent to the cell-binding agent in the cell-binding agent cytotoxic agent conjugate is about 1 to about 10, about 2 to about 7, about 3 to about 5, about 2.5 to about 4.5 (e.g., about 2.5, about 2.6, about 2.7, about 2.8, about 2.9, about 3.0, about 3.1, about 3.3, about 3.4, about 3.5, about 3.6, about 3.7, about 3.8, about 3.9, about 4.0, about 4.1, about 4.2, about 4.3, about 4.4, about 4.5), about 3.0 to about 4.0, about 3.2 to about 4.2, or about 4.5 to 5.5 (e.g., about 4.5, about 4.6, about 4.7, about 4.8, about 4.9, about 5.0, about 5.1, about 5.2, about 5.3, about 5.4, or about 5.5).

The present invention provides a more efficient process for preparing compositions of stable conjugates comprising a cell-binding agent chemically coupled to a cytotoxic agent. In one embodiment, as compared to the traditional processes for preparing conjugates of a cell-binding agent and a cytotoxic agent, less amount of the cytotoxic agent is required to achieve the same average molar ratio of the cytotoxic agent to the cell-binding agent for the conjugates.

The cell-binding agent can be any suitable agent that binds to a cell, typically and preferably an animal cell (e.g., a human cell). The cell-binding agent preferably is a peptide or a polypeptide. Suitable cell-binding agents include, for example, antibodies (e.g., monoclonal antibodies and fragments thereof), interferons (e.g. alpha., beta., gamma.), lymphokines (e.g., IL-2, IL-3, IL-4, IL-6), hormones (e.g., insulin, TRH (thyrotropin releasing hormone), MSH (melanocyte-stimulating hormone), steroid hormones, such as androgens and estrogens), growth factors and colony-stimulating factors such as EGF, TGF-alpha, FGF, VEGF, G-CSF, M-CSF and GM-CSF (Burgess, *Immunology Today* 5:155-158 (1984)), nutrient-transport molecules (e.g., transferrin), vitamins (e.g., folate) and any other agent or molecule that specifically binds a target molecule on the surface of a cell.

Where the cell-binding agent is an antibody, it binds to an antigen that is a polypeptide or a glycotope and may be a transmembrane molecule (e.g., receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-$\beta$; platelet-derived growth factor (PDGF); fibroblast growth factor such as aFGF and bFGF; epidermal growth factor (EGF); transforming growth factor (TGF) such as TGF-alpha and TGF-beta, including TGF-$\beta$1, TGF-$\beta$2, TGF-$\beta$3, TGF-$\beta$4, or TGF-$\beta$5; insulin-like growth factor-I and -II (IGF-I and IGF-II); des(1-3)-IGF-I (brain IGF-I); insulin-like growth factor binding proteins; EpCAM; GD3; FLT3; PSMA; PSCA; MUC1; MUC16; STEAP; CEA; TENB2; EphA receptors; EphB receptors; folate receptor; FOLR1; mesothelin; crypto; alpha$_v$beta$_6$; integrins; VEGF, VEGFR; EGFR; transferrin receptor; IRTA1; IRTA2; IRTA3; IRTA4; IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in U.S. Patent Application Publication No. 2008/0171040 or U.S. Patent Application Publication No. 2008/0305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3, or HER4 receptor; endoglin; c-Met; IGF1R; prostate antigens such as PCA3, PSA, PSGR, NGEP, PSMA, PSCA, TMEFF2, and STEAP1; LGR5; B7H4; and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma, as can antibodies directed towards melanomas. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents The term "antibody," as used herein, refers to any immunoglobulin, any immunoglobulin fragment, such as Fab, Fab', F(ab')$_2$, dsFv, sFv, minibodies, diabodies, tribodies, tetrabodies (Parham, *J. Immunol.*, 131: 2895-2902 (1983); Spring et al. *J. Immunol.*, 113: 470-478 (1974); Nisonoff et al. *Arch. Biochem. Biophys.*, 89: 230-244 (1960), Kim et al., *Mol. Cancer Ther.*, 7: 2486-2497 (2008), Carter, *Nature Revs.*, 6: 343-357 (2006)), or immunoglobulin chimera, which can bind to an antigen on the surface of a cell (e.g., which contains a complementarity determining region (CDR)). Any suitable antibody can be used as the cell-binding agent. One of ordinary skill in the art will appreciate that the selection of an appropriate antibody will depend upon the cell population to be targeted. In this regard, the type and number of cell surface molecules (i.e., antigens) that are selectively expressed in a particular cell population (typically and preferably a diseased cell population) will govern the selection of an appropriate antibody for use in the inventive composition. Cell surface expression profiles are known for a wide variety of cell types, including tumor cell types, or, if unknown, can be determined using routine molecular biology and histochemistry techniques.

The antibody can be polyclonal or monoclonal, but is most preferably a monoclonal antibody. As used herein, "polyclonal" antibodies refer to heterogeneous populations of antibody molecules, typically contained in the sera of immunized animals. "Monoclonal" antibodies refer to homogenous populations of antibody molecules that are specific to a particular antigen. Monoclonal antibodies are typically produced by a single clone of B lymphocytes ("B cells"). Monoclonal antibodies may be obtained using a variety of techniques known to those skilled in the art, including standard hybridoma technology (see, e.g., Köhler and Milstein, *Eur. J. Immunol.*, 5: 511-519 (1976), Harlow and Lane (eds.), *Antibodies: A Laboratory Manual*, CSH Press (1988), and C. A. Janeway et al. (eds.), *Immunobiology*, 5$^{th}$ Ed., Garland Publishing, New York, N.Y. (2001)). In brief, the hybridoma method of producing monoclonal antibodies typically involves injecting any suitable animal, typically and preferably a mouse, with an antigen (i.e., an "immunogen"). The animal is subsequently sacrificed, and B cells isolated from its spleen are fused with human myeloma cells. A hybrid cell is produced (i.e., a "hybridoma"), which proliferates indefinitely and continuously secretes high titers of an antibody with the desired specificity in vitro. Any appropriate method known in the art can be used to identify hybridoma cells that produce an antibody with the desired specificity. Such methods include, for example, enzyme-linked immunosorbent assay (ELISA), Western blot analysis, and radioimmunoassay. The population of hybridomas is screened to isolate individual clones, each of which secretes a single antibody species to the antigen. Because each hybridoma is a clone derived from fusion with a single B cell, all the antibody molecules it produces are identical in structure, including their antigen binding site and isotype. Monoclonal antibodies also may be generated using other suitable techniques including EBV-hybridoma technology (see, e.g., Haskard and Archer, *J. Immunol. Methods*, 74(2): 361-67 (1984), and Roder et al., *Methods Enzymol.*, 121: 140-67 (1986)), bacteriophage vector expression systems (see, e.g., Huse et al., *Science,* 246: 1275-81 (1989)), or phage display libraries comprising antibody fragments, such as Fab and scFv (single chain variable region) (see, e.g., U.S. Pat. Nos. 5,885,793 and 5,969,108, and International Patent Application Publications WO 92/01047 and WO 99/06587).

The monoclonal antibody can be isolated from or produced in any suitable animal, but is preferably produced in a mammal, more preferably a mouse or human, and most preferably a human. Methods for producing an antibody in mice are well known to those skilled in the art and are described herein. With respect to human antibodies, one of ordinary skill in the art will appreciate that polyclonal antibodies can be isolated from the sera of human subjects vaccinated or immunized with an appropriate antigen. Alternatively, human antibodies can be generated by adapting known techniques for producing human antibodies in non-human animals such as mice (see, e.g., U.S. Pat. Nos. 5,545,806, 5,569,825, and 5,714,352, and U.S. Patent Application Publication No. 2002/0197266 A1).

While being the ideal choice for therapeutic applications in humans, human antibodies, particularly human monoclonal antibodies, typically are more difficult to generate than mouse monoclonal antibodies. Mouse monoclonal antibodies, however, induce a rapid host antibody response when administered to humans, which can reduce the therapeutic or diagnostic potential of the antibody-cytotoxic agent conjugate. To circumvent these complications, a monoclonal antibody preferably is not recognized as "foreign" by the human immune system.

To this end, phage display can be used to generate the antibody. In this regard, phage libraries encoding antigen-binding variable (V) domains of antibodies can be generated using standard molecular biology and recombinant DNA techniques (see, e.g., Sambrook et al. (eds.), *Molecular Cloning, A Laboratory Manual,* 3$^{rd}$ Edition, Cold Spring Harbor Laboratory Press, New York (2001)). Phage encoding a variable region with the desired specificity are selected for specific binding to the desired antigen, and a complete human antibody is reconstituted comprising the selected variable domain. Nucleic acid sequences encoding the reconstituted antibody are introduced into a suitable cell line, such as a myeloma cell used for hybridoma production, such that human antibodies having the characteristics of monoclonal antibodies are secreted by the cell (see, e.g., Janeway et al., supra, Huse et al., supra, and U.S. Pat. No. 6,265,150). Alternatively, monoclonal antibodies can be generated from mice that are transgenic for specific human heavy and light chain immunoglobulin genes. Such methods are known in the art and described in, for example, U.S. Pat. Nos. 5,545,806 and 5,569,825, and Janeway et al., supra.

Most preferably the antibody is a humanized antibody. As used herein, a "humanized" antibody is one in which the complementarity-determining regions (CDR) of a mouse monoclonal antibody, which form the antigen binding loops of the antibody, are grafted onto the framework of a human antibody molecule. Owing to the similarity of the frameworks of mouse and human antibodies, it is generally accepted in the art that this approach produces a monoclonal antibody that is antigenically identical to a human antibody but binds the same antigen as the mouse monoclonal antibody from which the CDR sequences were derived. Methods for generating humanized antibodies are well known in the art and are described in detail in, for example, Janeway et al., supra, U.S. Pat. Nos. 5,225,539, 5,585,089 and 5,693,761, European Patent No. 0239400 B1, and United Kingdom Patent No. 2188638. Humanized antibodies can also be generated using the antibody resurfacing technology described in U.S. Pat. No. 5,639,641 and Pedersen et al., *J. Mol. Biol.,* 235: 959-973 (1994). While the antibody employed in the conjugate of the inventive composition most preferably is a humanized monoclonal antibody, a human monoclonal antibody and a mouse monoclonal antibody, as described above, are also within the scope of the invention.

Antibody fragments that have at least one antigen binding site, and thus recognize and bind to at least one antigen or receptor present on the surface of a target cell, also are within the scope of the invention. In this respect, proteolytic cleavage of an intact antibody molecule can produce a variety of antibody fragments that retain the ability to recognize and bind antigens. For example, limited digestion of an antibody molecule with the protease papain typically produces three fragments, two of which are identical and are referred to as the Fab fragments, as they retain the antigen binding activity of the parent antibody molecule. Cleavage of an antibody molecule with the enzyme pepsin normally produces two antibody fragments, one of which retains both antigen-binding arms of the antibody molecule, and is thus referred to as the F(ab')$_2$ fragment. Reduction of a F(ab')$_2$ fragment with dithiothreitol or mercaptoethylamine produces a fragment referred to as a Fab' fragment. A single-chain variable region fragment (sFv) antibody fragment, which consists of a truncated Fab fragment comprising the variable (V) domain of an antibody heavy chain linked to a V domain of a light antibody chain via a synthetic peptide, can be generated using routine recombinant DNA technology techniques (see, e.g., Janeway et al., supra). Similarly, disulfide-stabilized variable region fragments (dsFv) can be prepared by recombinant DNA technology (see, e.g., Reiter et al., *Protein Engineering,* 7: 697-704 (1994)). Antibody fragments in the context of the invention, however, are not limited to these exemplary types of antibody fragments. Any suitable antibody fragment that recognizes and binds to a desired cell surface receptor or antigen can be employed. Antibody fragments are further described in, for example, Parham, *J. Immunol.,* 131: 2895-2902 (1983), Spring et al., *J. Immunol.,* 113: 470-478 (1974), and Nisonoff et al., *Arch. Biochem. Biophys.,* 89: 230-244 (1960). Antibody-antigen binding can be assayed using any suitable method known in the art, such as, for example, radioimmunoassay (RIA), ELISA, Western blot, immunoprecipitation, and competitive inhibition assays (see, e.g., Janeway et al., supra, and U.S. Patent Application Publication No. 2002/0197266 A1).

In addition, the antibody can be a chimeric antibody or an antigen binding fragment thereof. By "chimeric" it is meant that the antibody comprises at least two immunoglobulins, or fragments thereof, obtained or derived from at least two different species (e.g., two different immunoglobulins, such as a human immunoglobulin constant region combined with a murine immunoglobulin variable region). The antibody also can be a domain antibody (dAb) or an antigen binding fragment thereof, such as, for example, a camelid antibody (see, e.g., Desmyter et al., *Nature Struct. Biol.,* 3: 752, (1996)), or a shark antibody, such as, for example, a new antigen receptor (IgNAR) (see, e.g., Greenberg et al., *Nature,* 374: 168 (1995), and Stanfield et al., *Science,* 305: 1770-1773 (2004)).

Any suitable antibody can be used in the context of the invention. For example, the monoclonal antibody J5 is a murine IgG2a antibody that is specific for Common Acute Lymphoblastic Leukemia Antigen (CALLA) (Ritz et al., *Nature,* 283: 583-585 (1980)), and can be used to target cells that express CALLA (e.g., acute lymphoblastic leukemia cells). The monoclonal antibody MY9 is a murine IgG1 antibody that binds specifically to the CD33 antigen (Griffin et al., *Leukemia Res.*, 8: 521 (1984)), and can be used to target cells that express CD33 (e.g., acute myelogenous leukemia (AML) cells).

Similarly, the monoclonal antibody anti-B4 (also referred to as B4) is a murine IgG1 antibody that binds to the CD19 antigen on B cells (Nadler et al., *J. Immunol.*, 131: 244-250 (1983)), and can be used to target B cells or diseased cells that express CD19 (e.g., non-Hodgkin's lymphoma cells and chronic lymphoblastic leukemia cells). N901 is a murine monoclonal antibody that binds to the CD56 (neural cell adhesion molecule) antigen found on cells of neuroendocrine origin, including small cell lung tumor, which can be used in the conjugate to target drugs to cells of neuroendocrine origin. The J5, MY9, and B4 antibodies preferably are resurfaced or humanized prior to their use as part of the conjugate. Resurfacing or humanization of antibodies is described in, for example, Roguska et al., *Proc. Natl. Acad. Sci. USA*, 91: 969-73 (1994).

In addition, the monoclonal antibody C242 binds to the CanAg antigen (see, e.g., U.S. Pat. No. 5,552,293), and can be used to target the conjugate to CanAg expressing tumors, such as colorectal, pancreatic, non-small cell lung, and gastric cancers. HuC242 is a humanized form of the monoclonal antibody C242 (see, e.g., U.S. Pat. No. 5,552,293). The hybridoma from which HuC242 is produced is deposited with ECACC identification Number 90012601. HuC242 can be prepared using CDR-grafting methodology (see, e.g., U.S. Pat. Nos. 5,585,089, 5,693,761, and 5,693,762) or resurfacing technology (see, e.g., U.S. Pat. No. 5,639,641). HuC242 can be used to target the conjugate to tumor cells expressing the CanAg antigen, such as, for example, colorectal, pancreatic, non-small cell lung, and gastric cancer cells.

To target ovarian cancer and prostate cancer cells, an anti-MUC1 antibody can be used as the cell-binding agent in the conjugate. Anti-MUC1 antibodies include, for example, anti-HMFG-2 (see, e.g., Taylor-Papadimitriou et al., *Int. J. Cancer*, 28: 17-21 (1981)), hCTMO1 (see, e.g., van H of et al., *Cancer Res.*, 56: 5179-5185 (1996)), and DS6. Prostate cancer cells also can be targeted with the conjugate by using an anti-prostate-specific membrane antigen (PSMA) as the cell-binding agent, such as J591 (see, e.g., Liu et al., *Cancer Res.*, 57: 3629-3634 (1997)). Moreover, cancer cells that express the Her2 antigen, such as breast, prostate, and ovarian cancers, can be targeted with the conjugate by using anti-Her2 antibodies, e.g., trastuzumab, as the cell-binding agent. Cells that express epidermal growth factor receptor (EGFR) and variants thereof, such as the type III deletion mutant, EGFRvIII, can be targeted with the conjugate by using anti-EGFR antibodies. Anti-EGFR antibodies are described in International Patent Application Nos. PCT/US11/058,385 and PCT/US11/058,378. Anti-EGFRvIII antibodies are described in U.S. Pat. Nos. 7,736,644 and 7,628,986 and U.S. Application Publications 2010/0111979, 2009/0240038, 2009/0175887, 2009/0156790, and 2009/0155282. Anti-IGF-IR antibodies that bind to insulin-like growth factor receptor, such as those described in U.S. Pat. No. 7,982,024, also can be used in the conjugate. Antibodies that bind to CD27L, Cripto, CD138, CD38, EphA2, integrins, CD37, folate, CD20, PSGR, NGEP, PSCA, TMEFF2, STEAP1, endoglin, and Her3 also can be used in the conjugate.

In one embodiment, the antibody is selected from the group consisting of huN901, huMy9-6, huB4, huC242, an anti-HER2 antibody (e.g., trastuzumab), bivatuzumab, sibrotuzumab, rituximab, huDS6, anti-mesothelin antibodies described in International Patent Application Publication WO 2010/124797 (such as MF-T), anti-cripto antibodies described in U.S. Patent Application Publication 2010/ 0093980 (such as huB3F6), anti-CD138 antibodies described in U.S. Patent Application Publication 2007/0183971 (such as huB-B4), anti-EGFR antibodies described in International Patent Application Nos. PCT/US11/058,385 and PCT/US11/058,378 (such as EGFR-7), anti-EGFRvIII antibodies described U.S. Pat. Nos. 7,736,644 and 7,628,986 and U.S. Patent Application Publications 2010/0111979, 2009/0240038, 2009/0175887, 2009/0156790 and 2009/0155282, humanized EphA2 antibodies described in International Patent Application Publications WO 2011/039721 and WO 2011/039724 (such as 2H11R35R74); anti-CD38 antibodies described in International Patent Application Publication WO 2008/047242 (such as hu38SB19), anti-folate antibodies described in International Patent Application Publication WO 2011/106528, and U.S. Patent Application Publication 2012/0009181 (e.g., huMov19); anti-IGF1R antibodies described in U.S. Pat. Nos. 5,958,872, 6,596,743, and 7,982,024; anti-CD37 antibodies described in U.S. Patent Application Publication 2011/0256153 (e.g., huCD37-3); anti-integrin $\alpha_v\beta_6$ antibodies described in U.S. Application Publication 2006/0127407 (e.g., CNTO95); and anti-Her3 antibodies described in International Patent Application Publication WO 2012/019024.

Particularly preferred antibodies are humanized monoclonal antibodies described herein. Examples include, but are not limited to, huN901, huMy9-6, huB4, huC242, a humanized monoclonal anti-Her2 antibody (e.g., trastuzumab), bivatuzumab, sibrotuzumab, CNTO95, huDS6, and rituximab (see, e.g., U.S. Pat. Nos. 5,639,641 and 5,665,357, U.S. Provisional Patent Application No. 60/424,332 (which is related to U.S. Pat. No. 7,557,189), International (PCT) Patent Application Publication WO 02/16401, Pedersen et al., supra, Roguska et al., supra, Liu et al., supra, Nadler et al., supra, Colomer et al., *Cancer Invest.*, 19: 49-56 (2001), Heider et al., *Eur. J. Cancer*, 31A: 2385-2391 (1995), Welt et al., *J. Clin. Oncol.*, 12: 1193-1203 (1994), and Maloney et al., *Blood*, 90: 2188-2195 (1997)). Other humanized monoclonal antibodies are known in the art and can be used in connection with the invention.

In one embodiment, the cell-binding agent is an humanized anti-folate antibody or antigen binding fragment thereof that specifically binds a human folate receptor 1, wherein the antibody comprises: (a) a heavy chain CDR1 comprising GYFMN (SEQ ID NO: 1); a heavy chain CDR2 comprising RIHPYDGDTFYNQXaa$_1$FXaa$_2$Xaa$_3$ (SEQ ID NO: 2); and a heavy chain CDR3 comprising YDGSRAMDY (SEQ ID NO: 3); and (b) a light chain CDR1 comprising KASQSVSF-AGTSLMH (SEQ ID NO: 4); a light chain CDR2 comprising RASNLEA (SEQ ID NO: 5); and a light chain CDR3 comprising QQSREYPYT (SEQ ID NO: 6); wherein Xaa$_1$ is selected from K, Q, H, and R; Xaa$_2$ is selected from Q, H, N, and R; and Xaa$_3$ is selected from G, E, T, S, A, and V. Preferably, the heavy chain CDR2 sequence comprises RIH-PYDGDTFYNQKFQG (SEQ ID NO: 7).

In another embodiment, the anti-folate antibody is a humanized antibody or antigen binding fragment thereof that specifically binds the human folate receptor 1 comprising the heavy chain having the amino acid sequence of

```
                                              (SEQ ID NO: 8)
QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD

GSRAMDYWGQGTTVTVSSASTKGPSVFPLAPSSKSTSGGTAALGCLVKDY
```

-continued

```
FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYNST

YRVVSVLTVLHQDWLNGKEYKCKVSNKALPAPIEKTISKAKGQPREPQVY

TLPPSRDELTKNQVSLTCLVKGFYPSDIAVEWESNGQPENNYKTTPPVLD

SDGSFFLYSKLTVDKSRWQQGNVFSCSVMHEALHNHYTQKSLSLSPGK.
```

In another embodiment, the anti-folate antibody is a humanized antibody or antigen binding fragment thereof encoded by the plasmid DNA deposited with the ATCC on Apr. 7, 2010 and having ATCC deposit nos. PTA-10772 and PTA-10773 or 10774.

In another embodiment, the anti-folate antibody is a humanized antibody or antigen binding fragment thereof comprising a heavy chain variable domain at least about 90%, 95%, 99% or 100% identical to

```
                                        (SEQ ID NO: 9)
QVQLVQSGAEVVKPGASVKISCKASGYTFTGYFMNWVKQSPGQSLEWIGR

IHPYDGDTFYNQKFQGKATLTVDKSSNTAHMELLSLTSEDFAVYYCTRYD

GSRAMDYWGQGTTVTVSS,
``` and a light chain variable domain at least about 90%, 95%, 99% or 100% identical to

```
                                        (SEQ ID NO: 10)
DIVLTQSPLSLAVSLGQPAIISCKASQSVSFAGTSLMHWYHQKPGQQPRL

LIYRASNLEAGVPDRFSGSGSKTDFTLNISPVEAEDAATYYCQQSREYPY

TFGGGTKLEIKR;
or
                                        (SEQ ID NO: 11)
DIVLTQSPLSLAVSLGQPAIISCKASQSVSFAGTSLMHWYHQKPGQQPRL

LIYRASNLEAGVPDRFSGSGSKTDFTLTISPVEAEDAATYYCQQSREYPY

TFGGGTKLEIKR.
```

While the cell-binding agent preferably is an antibody, the cell-binding agent also can be a non-antibody molecule. Suitable non-antibody molecules include, for example, interferons (e.g., alpha, beta, or gamma interferon), lymphokines (e.g., interleukin 2 (IL-2), IL-3, IL-4, or IL-6), hormones (e.g., insulin), growth factors (e.g., EGF, TGF-alpha, FGF, and VEGF), colony-stimulating factors (e.g., G-CSF, M-CSF, and GM-CSF (see, e.g., Burgess, *Immunology Today*, 5: 155-158 (1984)), somatostatin, and transferrin (see, e.g., O'Keefe et al., *J. Biol. Chem.*, 260: 932-937 (1985)). For example, GM-CSF, which binds to myeloid cells, can be used as a cell-binding agent to target acute myelogenous leukemia cells. In addition, IL-2, which binds to activated T-cells, can be used for prevention of transplant graft rejection, for therapy and prevention of graft-versus-host disease, and for treatment of acute T-cell leukemia. Epidermal growth factor (EGF) can be used to target squamous cancers such as lung cancer and head and neck cancer. Somatostatin can be used to target neuroblastoma cells and other tumor cell types.

The conjugate can comprise any suitable cytotoxic agents. A "cytotoxic agent," as used herein, refers to any compound that results in the death of a cell, induces cell death, or decreases cell viability. Suitable cytotoxic agents include, for example, maytansinoids and conjugatable ansamitocins (see, for example, International Patent Application No. PCT/US11/59131, filed Nov. 3, 2011), taxoids, CC-1065 and CC-1065 analogs, and dolastatin and dolastatin analogs. In a preferred embodiment of the invention, the cytotoxic agent is a maytansinoid, including maytansinol and maytansinol analogs. Maytansinoids are compounds that inhibit microtubule formation and are highly toxic to mammalian cells. Examples of suitable maytansinol analogues include those having a modified aromatic ring and those having modifications at other positions. Such maytansinoids are described in, for example, U.S. Pat. Nos. 4,256,746, 4,294,757, 4,307,016, 4,313,946, 4,315,929, 4,322,348, 4,331,598, 4,361,650, 4,362,663, 4,364,866, 4,424,219, 4,371,533, 4,450,254, 5,475,092, 5,585,499, 5,846,545, and 6,333,410.

Examples of maytansinol analogs having a modified aromatic ring include: (1) C-19-dechloro (U.S. Pat. No. 4,256,746) (prepared by LAH reduction of ansamytocin P2), (2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH), and (3) C-20-demethoxy, C-20-acyloxy (—OCOR), +/−dechloro (U.S. Pat. No. 4,294,757) (prepared by acylation using acyl chlorides).

Examples of maytansinol analogs having modifications of positions other than an aromatic ring include: (1) C-9-SH (U.S. Pat. No. 4,424,219) (prepared by the reaction of maytansinol with $H_2S$ or $P_2S_5$), (2) C-14-alkoxymethyl (demethoxy/$CH_2OR$) (U.S. Pat. No. 4,331,598), (3) C-14-hydroxymethyl or acyloxymethyl ($CH_2OH$ or $CH_2OAc$) (U.S. Pat. No. 4,450,254) (prepared from *Nocardia*), (4) C-15-hydroxy/acyloxy (U.S. Pat. No. 4,364,866) (prepared by the conversion of maytansinol by *Streptomyces*), (5) C-15-methoxy (U.S. Pat. Nos. 4,313,946 and 4,315,929) (isolated from *Trewia nudiflora*), (6) C-18-N-demethyl (U.S. Pat. Nos. 4,362,663 and 4,322,348) (prepared by the demethylation of maytansinol by *Streptomyces*), and (7) 4,5-deoxy (U.S. Pat. No. 4,371,533) (prepared by the titanium trichloride/LAH reduction of maytansinol).

In a preferred embodiment of the invention, the conjugate utilizes the thiol-containing maytansinoid DM1, also known as $N^{2'}$-deacetyl-$N^{2'}$-(3-mercapto-1-oxopropyl)-maytansine, as the cytotoxic agent. The structure of DM1 is represented by formula (I):

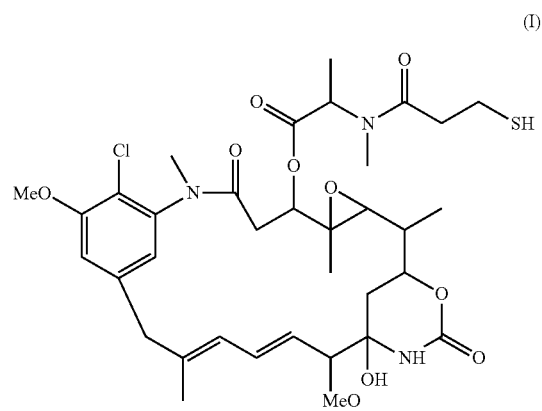 [SMILES: COc1cc2cc(c1Cl)N(C)C(=O)CC(OC(=O)C(C)N(C)C(=O)CCS)C1(C)OC1C(C)C1CC(O)(NC(=O)O1)C(OC)/C=C/C=C(\C)C2]

(I)

In another preferred embodiment of the invention, the conjugate utilizes the thiol-containing maytansinoid DM4, also known as $N^{2'}$-deacetyl-$N^{2'}$-(4-methyl-4-mercapto-1-oxopentyl)-maytansine, as the cytotoxic agent. The structure of DM4 is represented by formula (II):

(II)

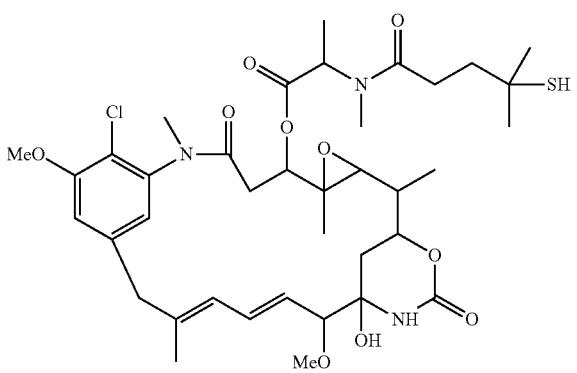

Other maytansinoids may be used in the context of the invention, including, for example, thiol and disulfide-containing maytansinoids bearing a mono or di-alkyl substitution on the carbon atom bearing the sulfur atom. Particularly preferred is a maytansinoid having at the C-3 position (a) C-14 hydroxymethyl, C-15 hydroxy, or C-20 desmethyl functionality, and (b) an acylated amino acid side chain with an acyl group bearing a hindered sulfhydryl group, wherein the carbon atom of the acyl group bearing the thiol functionality has one or two substituents, said substituents being $CH_3$, $C_2H_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocycloalkyl radical, and further wherein one of the substituents can be H, and wherein the acyl group has a linear chain length of at least three carbon atoms between the carbonyl functionality and the sulfur atom.

Additional maytansinoids for use in the context of the invention include compounds represented by formula (III):

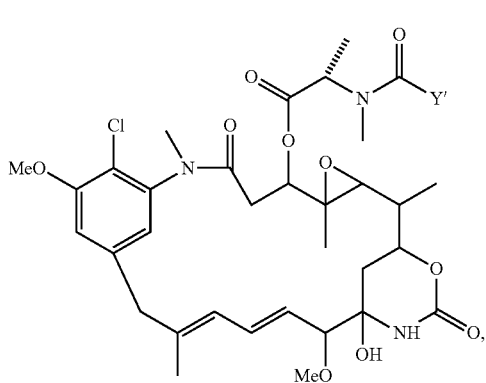

(III)

wherein Y' represents
$(CR_7R_8)_l(CR_9=CR_{10})_p(C\equiv C)_qA_o(CR_5R_6)_mD_u$
$(CR_{11}=CR_{12})_r(C\equiv C)_sB_t(CR_3R_4)_nCR_1R_2SZ$,
wherein $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein A, B, D are cycloalkyl or cycloalkenyl having 3-10 carbon atoms, simple or substituted aryl, or heterocyclic aromatic, or heterocycloalkyl radical, wherein $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic, or heterocycloalkyl radical, wherein l, m, n, o, p, q, r, s, and t are each independently zero or an integer from 1 to 5, provided that at least two of l, m, n, o, p, q, r, s and t are not zero at any one time, and wherein Z is H, SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic, or heterocycloalkyl radical.

Preferred embodiments of formula (III) include compounds of formula (III) wherein (a) $R_1$ is H, $R_2$ is methyl and Z is H, (b) $R_1$ and $R_2$ are methyl and Z is H, (c) $R_1$ is H, $R_2$ is methyl, and Z is —$SCH_3$, and (d) $R_1$ and $R_2$ are methyl, and Z is —$SCH_3$.

Such additional maytansinoids also include compounds represented by formula (IV-L), (IV-D), or (IV-D,L):

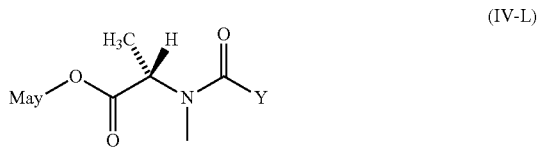

(IV-L)

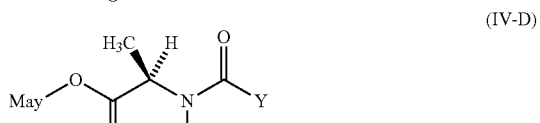

(IV-D)

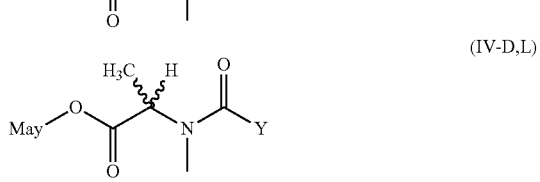

(IV-D,L)

wherein Y represents $(CR_7R_8)_l(CR_5R_6)_m(CR_3R_4)_n$ $CR_1R_2SZ$, wherein $R_1$ and $R_2$ are each independently $CH_3$, $C_2H_5$, linear alkyl, or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, wherein l, m, and n are each independently an integer of from 1 to 5, and in addition n can be zero, wherein Z is H, SR, or COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocycloalkyl radical, and wherein May represents a maytansinoid which bears the side chain at C-3, C-14 hydroxymethyl, C-15 hydroxy, or C-20 desmethyl.

Preferred embodiments of formulas (IV-L), (IV-D) and (IV-D,L) include compounds of formulas (IV-L), (IV-D) and (IV-D,L) wherein (a) $R_1$ is H, $R_2$ is methyl, $R_5$, $R_6$, $R_7$, and $R_8$ are each H, l and m are each 1, n is 0, and Z is H, (b) $R_1$ and $R_2$ are methyl, $R_5$, $R_6$, $R_7$, $R_8$ are each H, l and m are 1, n is 0, and Z is H, (c) $R_1$ is H, $R_2$ is methyl, $R_5$, $R_6$, $R_7$, and $R_8$ are each H, l and m are each 1, n is 0, and Z is —SCH₃, or (d) R₁ and R₂ are methyl, R₅, R₆, R₇, R₈ are each H, l and m are 1, n is 0, and Z is —SCH₃.

Preferably the cytotoxic agent is represented by formula (IV-L).

Additional preferred maytansinoids also include compounds represented by formula (V):

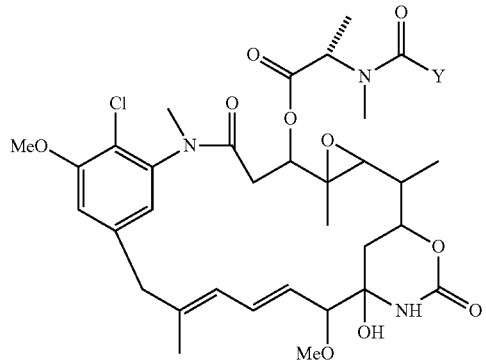

(V)

wherein Y represents $(CR_7R_8)_l(CR_5R_6)_m(CR_3R_4)_n CR_1R_2SZ$, wherein $R_1$ and $R_2$ are each independently $CH_3$, $C_2H_5$, linear alkyl, or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocycloalkyl radical, wherein l, m, and n are each independently an integer of from 1 to 5, and in addition n can be zero, and wherein Z is H, SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (V) include compounds of formula (V) wherein (a) $R_1$ is H, $R_2$ is methyl, $R_5$, $R_6$, $R_7$, and $R_8$ are each H; l and m are each 1; n is 0; and Z is H, (b) $R_1$ and $R_2$ are methyl; $R_5$, $R_6$, $R_7$, $R_8$ are each H, l and m are 1; n is 0; and Z is H, (c) $R_1$ is H, $R_2$ is methyl, $R_5$, $R_6$, $R_7$, and $R_8$ are each H, l and m are each 1, n is 0, and Z is —SCH₃, or (d) $R_1$ and $R_2$ are methyl, $R_5$, $R_6$, $R_7$, $R_8$ are each H, l and m are 1, n is 0, and Z is —SCH₃.

Still further preferred maytansinoids include compounds represented by formula (VI-L), (VI-D), or (VI-D,L):

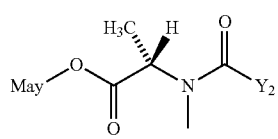

(VI-L)

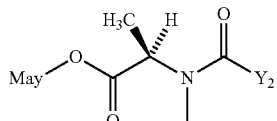

(VI-D)

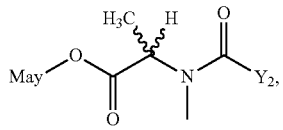

(VI-D,L)

wherein $Y_2$ represents $(CR_7R_8)_l(CR_5R_6)_m(CR_3R_4)_n CR_1R_2SZ_2$, wherein $R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, and wherein $R_2$ also can be H, wherein $R_3$, $R_4$, $R_5$, $R_6$, $R_7$, and $R_8$ are each independently H, $CH_3$, $C_2H_5$, linear cyclic alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, wherein l, m, and n are each independently an integer of from 1 to 5, and in addition n can be zero, wherein $Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical, and wherein May is the macrocyclic ring structure of the maytansinoid.

Additional preferred maytansinoids include compounds represented by formula (VII):

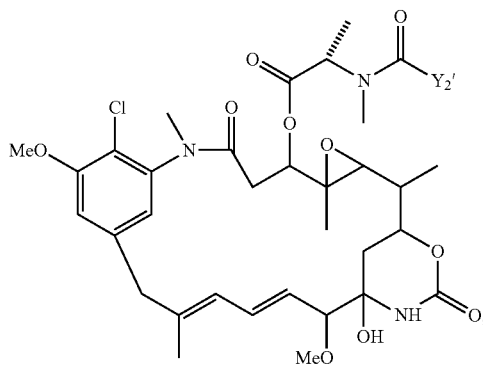

(VII)

wherein $Y_{2'}$ represents
$(CR_7R_8)_l(CR_9=CR_{10})_p(C\equiv C)_qA_o(CR_5R_6)_mD_u (CR_{11}=CR_{12})_r(C\equiv C)_sB_t(CR_3R_4)_nCR_1R_2SZ_2$, wherein $R_1$ and $R_2$ are each independently $CH_3$, $C_2H_5$, linear branched or alkyl or alkenyl having from 1 to 10 carbon atoms, cyclic alkyl or alkenyl having from 3 to 10 carbon atoms, phenyl, substituted phenyl or heterocyclic aromatic or heterocycloalkyl radical, and in addition $R_2$ can be H, wherein A, B, and D each independently is cycloalkyl or cycloalkenyl having 3 to 10 carbon atoms, simple or substituted aryl, or heterocyclic aromatic or heterocycloalkyl radical, wherein $R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocycloalkyl radical, wherein l, m, n, o, p, q, r, s, and t are each independently zero or an integer of from 1 to 5, provided that at least two of l, m, n, o, p, q, r, s and t are not zero at any one time, and wherein $Z_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocycloalkyl radical.

Preferred embodiments of formula (VII) include compounds of formula (VII), wherein $R_1$ is H and $R_2$ is methyl.

In addition to maytansinoids, the cytotoxic agent used in the conjugate can be a taxane or derivative thereof. Taxanes are a family of compounds that includes paclitaxel (Taxol®), a cytotoxic natural product, and docetaxel (Taxotere®), a semi-synthetic derivative, which are both widely used in the treatment of cancer. Taxanes are mitotic spindle poisons that inhibit the depolymerization of tubulin, resulting in cell death. While docetaxel and paclitaxel are useful agents in the treatment of cancer, their antitumor activity is limited because of their non-specific toxicity towards normal cells. Further, compounds like paclitaxel and docetaxel themselves are not sufficiently potent to be used in conjugates of cell-binding agents.

A preferred taxane for use in the preparation of a cytotoxic conjugate is the taxane of formula (VIII):

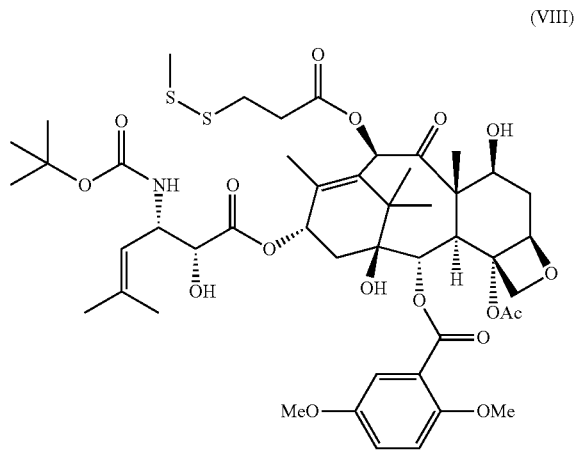 [SMILES: COc1ccc(OC)c(C(=O)O[C@H]2[C@@H]3[C@]4(OC(C)=O)CO[C@@H]4C[C@H](O)[C@@]3(C)C(=O)[C@H](OC(=O)CCSSC)C3=C(C)[C@@H](OC(=O)[C@H](O)[C@H](C=C(C)C)NC(=O)OC(C)(C)C)C[C@]2(O)C3(C)C)c1]

(VIII)

Methods for synthesizing taxanes that can be used in the context of the invention, along with methods for conjugating taxanes to cell-binding agents such as antibodies, are described in detail in U.S. Pat. Nos. 5,416,064, 5,475,092, 6,340,701, 6,372,738, 6,436,931, 6,596,757, 6,706,708, 6,716,821, and 7,390,898.

The cytotoxic also can be CC-1065 or a derivative thereof. CC-1065 is a potent anti-tumor antibiotic isolated from the culture broth of Streptomyces zelensis. CC-1065 is about 1000-fold more potent in vitro than commonly used anticancer drugs, such as doxorubicin, methotrexate, and vincristine (Bhuyan et al., Cancer Res., 42: 3532-3537 (1982)). CC-1065 and its analogs are disclosed in U.S. Pat. Nos. 5,585,499, 5,846,545, 6,340,701, and 6,372,738. The cytotoxic potency of CC-1065 has been correlated with its alkylating activity and its DNA-binding or DNA-intercalating activity. These two activities reside in separate parts of the molecule. In this respect, the alkylating activity is contained in the cyclopropapyrroloindole (CPI) subunit and the DNA-binding activity resides in the two pyrroloindole subunits of CC-1065.

Several CC-1065 analogs are known in the art and also can be used as the cytotoxic agent in the conjugate (see, e.g., Warpehoski et al., J. Med. Chem., 31: 590-603 (1988)). A series of CC-1065 analogs has been developed in which the CPI moiety is replaced by a cyclopropabenzindole (CBI) moiety (Boger et al., J. Org. Chem., 55: 5823-5833 (1990), and Boger et al., Bioorg. Med. Chem. Lett., 1: 115-120 (1991)). These CC-1065 analogs maintain the high in vitro potency of the parental drug, without causing delayed toxicity in mice. Like CC-1065, these compounds are alkylating agents that covalently bind to the minor groove of DNA to cause cell death.

The therapeutic efficacy of CC-1065 analogs can be greatly improved by changing the in vivo distribution through targeted delivery to a tumor site, resulting in lower toxicity to non-targeted tissues, and thus, lower systemic toxicity. To this end, conjugates of analogs and derivatives of CC-1065 with cell-binding agents that specifically target tumor cells have been generated (see, e.g., U.S. Pat. Nos. 5,475,092, 5,585, 499, and 5,846,545). These conjugates typically display high target-specific cytotoxicity in vitro, and anti-tumor activity in human tumor xenograft models in mice (see, e.g., Chari et al., Cancer Res., 55: 4079-4084 (1995)).

Methods for synthesizing CC-1065 analogs are described in detail in U.S. Pat. Nos. 5,475,092, 5,585,499, 5,846,545, 6,534,660, 6,586,618, 6,756,397, and 7,329,760.

Drugs such as methotrexate, daunorubicin, doxorubicin, vincristine, vinblastine, melphalan, mitomycin C, chlorambucil, calicheamicin, tubulysin and tubulysin analogs, duocarmycin and duocarmycin analogs, dolastatin and dolastatin analogs also can be used as the cytotoxic agent of the invention. Doxarubicin and daunorubicin compounds (see, e.g., U.S. Pat. No. 6,630,579) can also be used as the cytotoxic agent.

The cell-binding agent cytotoxic agent conjugates may be prepared by in vitro methods. In order to link a cytotoxic agent to the antibody, a linking group is used. Suitable linking groups are well known in the art and include disulfide groups, acid labile groups, photolabile groups, peptidase labile groups, and esterase labile groups, as well as noncleavable linking groups. For example, the cell binding agent can be chemically coupled to the cytotoxic agent via chemical bonds selected from the group consisting of disulfide bonds, acid labile bonds, photolabile bonds, peptidase labile bonds, thioether bonds, and esterase labile bonds.

In accordance with the invention, the cell-binding agent is linked with the cytotoxic agent via a bifunctional crosslinking reagent. As used herein, a "bifunctional crosslinking reagent" refers to a reagent that possesses two reactive groups; one of which is capable of reacting with a cell-binding agent, while the other one is capable of reacting with the cytotoxic agent to link the cell-binding agent with the cytotoxic agent, thereby forming a conjugate.

Any suitable bifunctional crosslinking reagent can be used in connection with the invention, so long as the linker reagent provides for retention of the therapeutic, e.g., cytotoxicity, and targeting characteristics of the cytotoxic agent and the cell-binding agent, respectively, without undue toxicity. Preferably, the linker molecule joins the cytotoxic agent to the cell-binding agent through chemical bonds (as described above), such that the cytotoxic agent and the cell-binding agent are chemically coupled (e.g., covalently bonded) to each other.

In one embodiment, the bifunctional crosslinking reagent comprises non-cleavable linkers. A non-cleavable linker is any chemical moiety that is capable of linking a cytotoxic agent, such as a maytansinoid, a taxane, or a CC-1065 analog, to a cell-binding agent in a stable, covalent manner. Thus, non-cleavable linkers are substantially resistant to acid-induced cleavage, light-induced cleavage, peptidase-induced cleavage, esterase-induced cleavage, and disulfide bond cleavage, at conditions under which the cytotoxic agent or the cell-binding agent remains active.

Suitable crosslinking reagents that form non-cleavable linkers between a cytotoxic agent and the cell-binding agent are well known in the art. In one embodiment, the cytotoxic agent is linked to the cell-binding agent through a thioether bond. Examples of non-cleavable linkers include linkers having a maleimido- or haloacetyl-based moiety for reaction with the cytotoxic agent. Such bifunctional crosslinking agents are well known in the art (see U.S. Patent Application Publication Nos. 2010/0129314, 2009/0274713, 2008/0050310, 20050169933, 2009/0274713, 2010/0129314, and those available from Pierce Biotechnology Inc. P.O. Box 117, Rockland, Ill. 61105, USA) and include, but not limited to, N-succinimidyl 4-(maleimidomethyl)cyclohexanecarboxylate (SMCC), N-succinimidyl-4-(N-maleimidomethyl)-cyclohexane-1-carboxy-(6-amidocaproate), which is a "long chain" analog of SMCC (LC-SMCC), κ-maleimidoundecanoic acid N-succinimidyl ester (KMUA), γ-maleimidobutyric acid N-succinimidyl ester (GMBS), ε-maleimidocaproic acid N-hydroxysuccinimide ester (EMCS), m-maleimidobenzoyl-N-hydroxysuccinimide ester (MBS), N-(α-maleimidoacetoxy)-succinimide ester (AMAS), succinimidyl-6-(β-maleimidopropionamido)hexanoate (SMPH), N-succinimidyl 4-(p-maleimidophenyl)-butyrate (SMPB), and N-(p-maleimidophenyl)isocyanate (PMPI). Cross-linking reagents comprising a haloacetyl-based moiety include N-succinimidyl-4-(iodoacetyl)-aminobenzoate (SIAB), N-succinimidyl iodoacetate (SIA), N-succinimidyl bromoacetate (SBA), and N-succinimidyl 3-(bromoacetamido)propionate (SBAP), bis-maleimidopolyethyleneglycol (BMPEO), BM(PEO)$_2$, BM(PEO)$_3$, N-(β-maleimidopropyloxy)succinimide ester (BMPS), 5-maleimidovaleric acid NHS, HBVS, 4-(4-N-maleimidophenyl)-butyric acid hydrazide.HCl (MPBH), Succinimidyl-(4-vinylsulfonyl)benzoate (SVSB), dithiobis-maleimidoethane (DTME),1,4-bis-maleimidobutane (BMB), 1,4 bismaleimidyl-2,3-dihydroxybutane (BMDB), bis-maleimidohexane (BMH), bis-maleimidoethane (BMOE), sulfosuccinimidyl 4-(N-maleimido-methyl)cyclohexane-1-carboxylate (sulfo-SMCC), sulfosuccinimidyl(4-iodo-acetyl)aminobenzoate (sulfo-SIAB), m-Maleimidobenzoyl-N-hydroxysulfosuccinimide ester (sulfo-MBS), N-(γ-maleimidobutryloxy)sulfosuccinimde ester (sulfo-GMBS), N-(ε-maleimidocaproyloxy) sulfosuccimido ester (sulfo-EMCS), maleimidoundecanoyloxy)sulfosuccinimide ester (sulfo-KMUS), sulfosuccinimidyl 4-(p-maleimidophenyl)butyrate (sulfo-SMPB), CX1-1, sulfo-Mal and PEG$_n$-Mal. Preferably, the bifunctional crosslinking reagent is SMCC.

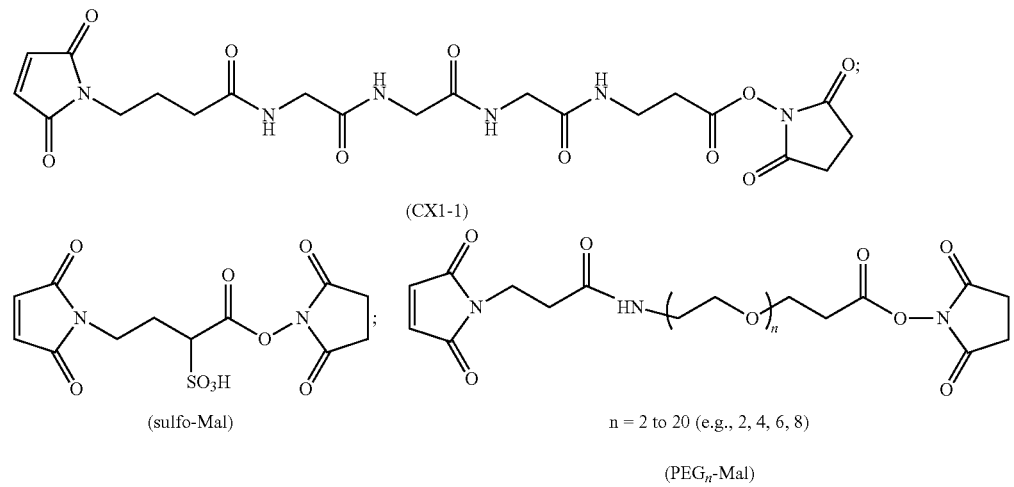

(CX1-1)

(sulfo-Mal)

n = 2 to 20 (e.g., 2, 4, 6, 8)

(PEG$_n$-Mal)

In one embodiment, the linking reagent is a cleavable linker. Examples of suitable cleavable linkers include disulfide linkers, acid labile linkers, photolabile linkers, peptidase labile linkers, and esterase labile linkers. Disulfide containing linkers are linkers cleavable through disulfide exchange, which can occur under physiological conditions. Acid labile linkers are linkers cleavable at acid pH. For example, certain intracellular compartments, such as endosomes and lysosomes, have an acidic pH (pH 4-5), and provide conditions suitable to cleave acid labile linkers. Photo labile linkers are useful at the body surface and in many body cavities that are accessible to light. Furthermore, infrared light can penetrate tissue. Peptidase labile linkers can be used to cleave certain peptides inside or outside cells (see e.g., Trouet et al., *Proc. Natl. Acad. Sci. USA*, 79: 626-629 (1982), and Umemoto et al., *Int. J. Cancer*, 43: 677-684 (1989)). In one embodiment, the cleavable linker is cleaved under mild conditions, i.e., conditions within a cell under which the activity of the cytotoxic agent is not affected.

In another embodiment, the cytotoxic agent is linked to a cell-binding agent through a disulfide bond. The linker molecule comprises a reactive chemical group that can react with the cell-binding agent. Preferred reactive chemical groups for reaction with the cell-binding agent are N-succinimidyl esters and N-sulfosuccinimidyl esters. Additionally the linker molecule comprises a reactive chemical group, preferably a dithiopyridyl group, that can react with the cytotoxic agent to form a disulfide bond. Bifunctional crosslinking reagents that enable the linkage of the cell-binding agent with the cytotoxic agent via disulfide bonds are known in the art and include, for example, N-succinimidyl 3-(2-pyridyldithio)propionate (SPDP) (see, e.g., Carlsson et al., *Biochem. J.,* 173: 723-737 (1978)), N-succinimidyl 4-(2-pyridyldithio)butanoate (SPDB) (see, e.g., U.S. Pat. No. 4,563,304), N-succinimidyl 4-(2-pyridyldithio)pentanoate (SPP) (see, e.g., CAS Registry number 341498-08-6), and N-succinimidyl-4-(2-pyridyldithio)-2-sulfo butanoate (sulfo-SPDB) (see, e.g., U.S. Application Publication 2009/0274713). Other bifunctional crosslinking reagents that can be used to introduce disulfide groups are known in the art and are described in U.S. Pat. Nos. 6,913,748, 6,716,821 and U.S. Patent Application Publications 2009/0274713 and 2010/0129314, all of which are incorporated herein in its entirety by reference.

Other crosslinking reagents lacking a sulfur atom that form non-cleavable linkers can also be used in the inventive method. Such linkers can be derived from dicarboxylic acid based moieties. Suitable dicarboxylic acid based moieties include, but are not limited to, α,ω-dicarboxylic acids of the general formula (IX):

$$HOOC-X_l-Y_n-Z_m-COOH \quad (IX),$$

wherein X is a linear or branched alkyl, alkenyl, or alkynyl group having 2 to 20 carbon atoms, Y is a cycloalkyl or cycloalkenyl group bearing 3 to 10 carbon atoms, Z is a substituted or unsubstituted aromatic group bearing 6 to 10 carbon atoms, or a substituted or unsubstituted heterocyclic group wherein the hetero atom is selected from N, O or S, and wherein l, m, and n are each 0 or 1, provided that l, m, and n are all not zero at the same time.

Many of the non-cleavable linkers disclosed herein are described in detail in U.S. Patent Application Publication No. 2005/0169933 A1.

The following examples further illustrate the invention but, of course, should not be construed as in any way limiting its scope.

EXAMPLE 1

Humanized CD37-3 antibody was reacted with the heterobifunctional crosslinking reagent SMCC and the maytansinoid DM1 using a previously described process (e.g. U.S. Pat. No. 5,208,020), as well as the one-step process that is the subject of the present application.

For the previously described process, huCD37-3 (15 mg/mL) first was reacted with SMCC (6.5-fold molar excess relative to the amount of antibody) to form the modified antibody. The modification reaction was performed at 16° C. in 50 mM sodium phosphate buffer (pH 6.9) containing 2 mM EDTA and 10% DMA for 90 minutes. The reaction was quenched with 1 M acetate to adjust the pH to 4.5 and the modified antibody was purified using a column of Sephadex G-25F resin equilibrated and eluted in 20 mM sodium acetate (pH 4.5) containing 2 mM EDTA. After purification, the modified antibody (5 mg/mL) was reacted with the maytansinoid DM1 (6.8-fold molar excess relative to the amount of antibody; 1.3-fold excess relative to the measured amount of linker on the antibody) to form the conjugated antibody. The conjugation reaction was performed at 20° C. in 20 mM sodium acetate buffer (pH 5.0) containing 2 mM EDTA and 5% DMA for approximately 20 hours. The reaction mixture was then purified using a column of Sephadex G-25F resin equilibrated and eluted in 10 mM sodium succinate (pH 5.0).

For the inventive process, huCD37-3 (2.5 mg/mL) was mixed with DM1 (6.2-fold molar excess relative to the amount of antibody) and then with SMCC (5.2-fold excess relative to the amount of antibody). The reaction was performed at 20° C. in 50 mM EPPS [4-(2-Hydroxyethyl)-1-piperazinepropanesulfonic acid] buffer (pH 8.1) containing 2 mM EDTA and 10% DMA for approximately 4 hours. The reaction was quenched by adding 1 M acetate to adjust the pH to 5.0. The reaction mixture was then held at 2-8° C. for approximately 20 hours. After holding, the reaction mixture was filtered through a 0.2 µm PVDF filter and purified and diafiltered into 10 mM sodium succinate (pH 5.0) using Tangential Flow Filtration (TFF).

Conjugate derived from the two processes was analyzed by: UV spectroscopy for concentration and cytotoxic agent loading (Maytansinoid to Antibody Ratio, MAR); Mass Spectrometry for determination of unconjugated linker level; reduced SDS PAGE electrophoresis for determination of level of non-reducible species; SEC-HPLC for determination of conjugate monomer; and stability on storage with respect to conjugate monomer and free maytansinoid release.

Concentration and Maytansinoid to Antibody Ratio (MAR) were determined by measuring the absorbance of the conjugate at 252 and 280 nm in a UV-VIS spectrophotometer and using the molar extinction coefficients of DM1 and antibody at the two wavelengths to calculate the molar concentrations of antibody and DM1.

The un-conjugated linker level of the conjugates was analyzed by mass spectrometry: peak areas of individual conjugate species (including conjugates with or without un-conjugated linkers) were measured; the un-conjugated linker level was calculated by the ratio of the sum of areas containing un-conjugated linkers (weighted by the number of linkers) to the sum of areas of all conjugate species (also weighted by the number of linkers).

The non-reducible species level of the conjugates was analyzed by reduced SDS gel electrophoresis: peak areas of individual reduced conjugate species (including reduced light chain, reduced heavy chain, cross-linked light-light chains, cross-linked light-heavy chains, etc.) were measured; the non-reducible species level was calculated by the ratio of the sum of areas of non-reducible species to the sum of areas of all species.

The monomer level of the conjugates was analyzed by size exclusion HPLC: peak areas of monomer, dimer, aggregates and low molecular weight species were measured using an absorbance detector set to a wavelength of 252 nm or 280 nm; the monomer level was calculated by the ratio of the monomer area to the total area.

The amount of free maytansinoid present in the conjugate was analyzed by dual column (HiSep and C18 columns) HPLC: peak areas of total free maytansinoid species (eluted in the gradient and identified by comparison of elution time with known standards) were measured using an absorbance detector set to a wavelength of 252 nm; the amount of free maytansinoid was calculated using a standard curve generated by the peak areas of known amount of standards.

As shown in Table 1 below, conjugate manufactured using the inventive process was superior to that manufactured using the previously described process with respect to unconjugated linker, non-reducible species, and conjugate monomer. In addition, the stability of conjugate made by the inventive process was significantly superior with respect to free maytansinoid release after storage for five months at 4° C. Monomer levels of conjugates made by both processes were stable.

TABLE 1

Comparison of key properties of CD37-3 conjugate manufactured by the inventive process compared to previous process

|  | Previous Process | Inventive Process |
|---|---|---|
| Conjugate concentration | 3.9 | 8.1 |
| Maytansinoid to Antibody ratio | 4.1 | 3.4 |
| Unconjugated Linker (%) | 12 | <1 |
| Nonreducible species (%) | 9.4 | 0.9 |
| Conjugate monomer, (%) (t = 0) | 97.8 | 98.9 |
| Conjugate monomer, (%) (after 5 months at 4° C.) | 97.8 | 98.4 |
| Free Maytansinoid, (%) (t = 0) | 0.4 | 0.2 |
| Free Maytansinoid, (%) (after 5 months at 4° C.) | 3.3 | 0.5 |

The results of the experiments reflected in this example demonstrate an improved processes for preparing cell-binding agent-cytotoxic agent conjugates that are of substantially high purity. In addition to the improvements in conjugate purity and stability from using the inventive process, there are also improvements in processing time and convenience, due to elimination of two processing steps (modification reaction and purification of the modified antibody).

EXAMPLE 2

Humanized Folate Receptor antibody huMov19 (see U.S. Application Publication 2012/0009181) was reacted with the heterobifunctional crosslinking reagent sulfo-SPDB and the maytansinoid DM4 using two previously described processes, as well as the improved process that is the subject of the present application.

For the previously described Process A (two-step process, e.g. Chari et al., U.S. Pat. No. 5,208,020), huMov19 antibody (20 mg/mL) first was reacted with sulfo-SPDB (5.7-fold molar excess relative to the amount of antibody, dissolved in DMA, dimethylacetamide) to form the modified antibody. The modification reaction was performed at 20° C. in 50 mM EPPS (4-(2-hydroxyethyl)piperazine-1-propanesulfonic acid) buffer (pH 8.1) containing 5% DMA for 180 minutes. The modified antibody was purified using a column of Sephadex G-25F resin equilibrated and eluted in 50 mM EPPS (pH 8.1) with 2 mM EDTA (Ethylenediaminetetraacetic acid). After purification, the modified antibody (5.0 mg/mL) was reacted with the maytansinoid DM4 (Dissolved in DMA; 9.7-fold molar excess relative to the amount of antibody; 1.7-fold excess relative to the measured amount of linker on the antibody) to form the conjugated antibody. The conjugation reaction was performed at room temperature in 50 mM EPPS (pH 8.1) containing 2 mM EDTA and 5% DMA for approximately 18 hours. The reaction mixture was then purified using a column of Sephadex G-25F resin equilibrated and eluted in 10 mM sodium succinate (pH 5.0).

For the previously described Process B (one-pot process, Dai et al., U.S. Pat. No. 7,811,572), huMov19 antibody (10 mg/mL) first was reacted with sulfo-SPDB (4.9-fold molar excess relative to the amount of antibody, dissolved in DMA) to form the modified antibody. The modification reaction was performed at 20° C. in 50 mM EPPS buffer (pH 7.5) containing 2 mM EDTA and 10% DMA for 60 minutes. The modified antibody was not purified before the conjugation reaction. Instead, the un-purified modified antibody was reacted at 10 mg/mL with the maytansinoid DM4 (8.3-fold molar excess relative to the amount of antibody, dissolved in DMA) to form the conjugated antibody. The conjugation reaction was performed at room temperature in 50 mM EPPS buffer (pH 7.5) containing 2 mM EDTA and 10% DMA for approximately 18 hours. The reaction mixture was then purified using a column of Sephadex G-25F resin equilibrated and eluted in 10 mM sodium succinate (pH 5.0).

For the inventive process in which Sephadex G-25 was used (Process C, one-step process) to purify the conjugate, huMov19 antibody (6.0 mg/mL) was mixed with DM4 (9.7-fold molar excess relative to the amount of antibody, dissolved in DMA) and then sulfo-SPDB (5.7-fold excess relative to the amount of antibody, dissolved in DMA) was added. The reaction was performed at 20° C. in 50 mM EPPS buffer (pH 8.1) containing 2 mM EDTA and 10% DMA for approximately 20 hours. The reaction mixture was then purified using a column of Sephadex G-25F resin equilibrated and eluted in 10 mM sodium succinate (pH 5.0).

For the inventive process in which tangential flow filtration (TFF) (Process D, one-step process) was used to purify the conjugate, huMov19 antibody (5.0 mg/mL) was mixed with DM4 (10.2-fold molar excess relative to the amount of antibody, dissolved in DMA) and then with sulfo-SPDB (6.0-fold excess relative to the amount of antibody, dissolved in DMA). The reaction was performed at 20° C. in 50 mM EPPS buffer (pH 8.5) containing 2 mM EDTA and 10% DMA for approximately 20 hours. The reaction mixture was then purified and diafiltered using a TFF into 10 mM sodium succinate (pH 5.0).

Conjugate derived from the different processes was analyzed by: UV spectroscopy (for concentration and maytansinoid to antibody ratio, MAR); reversed phase HPLC for determination of Free Maytansinoid; Mass Spectrometry for determination of unconjugated linker level and mass distribution profile; reduced SDS PAGE electrophoresis for determination of level of non-reducible species; non-reduced SDS PAGE electrophoresis for determination of level of fragmentation; SEC-HPLC for determination of conjugate monomer. Stability on storage was assessed with respect to conjugate monomer and free maytansinoid release. Additional details on the analytical methodologies are provided in Example 1.

As shown in Table 2 below, conjugate manufactured using the inventive process was superior to that manufactured using the previously described processes with respect to monomer. Conjugate manufactured using the one-pot and one-step processes in which the final purification of conjugate was performed using Sephadex G-25, Processes B and C, respectively, had a higher level of free maytansinoid than conjugate manufactured using the two step process, Process A. However, when a different final purification process, TFF, was used (Process D), the level of free maytansinoid was very low and comparable to that seen with the two-step process, both after initial purification and after storage at 4° C. for six weeks. With respect to other important conjugate attributes (e.g. fragmentation, non-reducible species, mass distribution profile and unconjugated linker), conjugate manufactured using the inventive process was equivalent to that manufactured by the previously described processes.

TABLE 2

Comparison of key properties of huMov19 conjugate manufactured by the inventive process compared to previous processes

| Process | Process A* | Process B* | Process C* | Process D** |
|---|---|---|---|---|
| Number of Unit Operations | 5 | 4 | 3 | 3 |
| Concentration (mg/mL) | 1.0 | 1.0 | 1.0 | 4.2 |
| MAR (UV) | 4 | 3.8 | 3.7 | 3.6 |
| Conjugate Monomer, (%) at t = 0 | 94.8 | 97.4 | 98.9 | 98.6 |
| Conjugate Monomer, (%) at t = 6 weeks, 4° C. | 94.4 | 97.5 | 98.8 | 98.1 |
| Free Maytansinoid, (%) at t = 0 | 0.6 | 6.3 | 3.1 | 0.1 |

TABLE 2-continued

Comparison of key properties of huMov19 conjugate manufactured by the inventive process compared to previous processes

| Process | Process A* | Process B* | Process C* | Process D** |
|---|---|---|---|---|
| Free Maytansinoid, (%) at t = 6 weeks, 4° C. | 0.6 | 5.4 | 2.7 | 0.4 |
| Fragmentation By non-reducing gel-chip (%) | 10 | 14 | 14 | 12 |
| Non-reducible species By reducing gel-chip (%) | 0.7 | 0.8 | 0.7 | 0.5 |
| Mass Distribution Profile (MDP) | Comparable | | | |
| Unconjugated Linker (MDP) | Non-Detectible | | | |

*Purified with Sephadex G-25
**Purified using TFF

The results of the experiments reflected in this example demonstrate an improved processes for preparing cell-binding agent-cytotoxic agent conjugates that are of substantially high purity. In addition to the improvements in conjugate purity and stability from using the inventive process, there are also improvements in processing time and convenience, due to elimination of two processing steps (modification reaction and purification of the modified antibody).

EXAMPLE 3

This example demonstrates that the one-step process described herein can be used to make conjugates starting with a variety of linkers and maytansinoid cytotoxic agents.

Humanized huN901 antibody was mixed with Maytansinoid (DM1 or DM4) and then with Linker (Sulfo-SMCC, SMCC, SPDB, or SPP). The reaction was performed at 20° C. in 50 mM phosphate buffer (pH 7.5) containing 2 mM EDTA and 10% DMA for approximately 20-24 hours. The reaction mixture was then purified using a column of Sephadex G25F resin equilibrated and eluted in 10 mM sodium succinate (pH 5.0).

As shown in Table 3 below, the one-step reaction can be performed on different linker and maytansinoid combinations and yield conjugate with good MAR and monomer levels.

TABLE 3

Making conjugates by using different linker and maytansinoid combinations

| | Linker | DMx | Conjugate MAR | Conjugate Monomer (%) |
|---|---|---|---|---|
| Two-step | SPP | DM1 | 3.5 | 96.8 |
| One-step | SPP | DM1 | 3.4 | 97.5 |
| (Inventive) | SPDB | DM1 | 4.6 | 97.7 |
| | SMCC | DM4 | 4.5 | 95.1 |
| | S-SMCC | DM1 | 3.5 | 98.0 |
| | SPDB | DM4 | 3.8 | 97.3 |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing an antibody maytansinoid conjugate comprising the step of:
   (a) contacting an antibody with a maytansinoid to form a first mixture comprising the antibody and the maytansinoid, then contacting the first mixture with a bifunctional crosslinking reagent comprising a linker, in a solution having a pH of about 4 to about 9 to provide a second mixture comprising (i) the antibody maytansinoid conjugate, wherein the antibody is chemically coupled through the linker to the maytansinoid, (ii) free maytansinoid, and (iii) reaction by-products.

2. The process of claim 1, wherein the process further comprises the step of:
   (b) purifying the second mixture comprising the antibody maytansinoid conjugate to provide a purified antibody maytansinoid conjugate.

3. The process of claim 2, wherein the second mixture is purified by subjecting the mixture to tangential flow filtration, selective precipitation, adsorptive filtration, adsorptive chromatography, non-absorptive chromatography, or a combination thereof, to purify the antibody maytansinoid conjugate from the free maytansinoid and reaction by-products.

4. The process of claim 3, wherein the second mixture is purified by subjecting the mixture to tangential flow filtration.

5. The process of claim 1, wherein the contacting in step (a) is effected by providing the antibody in a reaction vessel, adding the maytansinoid to the reaction vessel to form the first mixture comprising the antibody and the maytansinoid, and then adding the bifunctional crosslinking reagent to the first mixture.

6. The process of claim 2, further comprising holding the second mixture between steps (a)-(b) to release the unstably bound linkers from the antibody.

7. The process of claim 6, wherein the second mixture is held for about 20 hours at a temperature of about 2° C. to about 8° C.

8. The process of claim 2, further comprising quenching the second mixture between steps (a)-(b) to quench any unreacted maytansinoid and/or unreacted bifunctional crosslinking reagent.

9. The process of claim 8, wherein the mixture is quenched by contacting the second mixture with a quenching reagent that reacts with the free maytansinoid.

10. The process of claim 9, wherein the quenching reagent is selected from the group consisting of 4-maleimidobutyric acid, 3-maleimidopropionic acid, N-ethylmaleimide, iodoacetamide, and iodoacetamidopropionic acid.

11. The process of claim 1, wherein the contacting in step (a) occurs in a solution having a pH of about 7 to about 9.

12. The process of claim 1, wherein the contacting in step (a) occurs at a temperature of about 16° C. to about 24° C.

13. The process of claim 1, wherein the contacting in step (a) occurs at a temperature of about 0° C. to about 15° C.

14. The process of claim 1, wherein the antibody is a monoclonal antibody.

15. The process of claim 14, wherein the antibody is a humanized monoclonal antibody.

16. The process of claim 1, wherein the antibody is selected from the group consisting of huN901, huMy9-6, huB4, huC242, trastuzumab, bivatuzumab, sibrotuzumab, CNTO95, huDS6, rituximab, an antibody that binds to Her2, an antibody that binds to epidermal growth factor receptor (EGFR), an antibody that binds to CD27L, an antibody that binds to EGFRvIII, an antibody that binds to Cripto, an antibody that binds to CD138, an antibody that binds to EphA2, an integrin targeting antibody, an antibody that binds to CD37, an antibody that binds to folate, an antibody that binds to Her3, and an antibody that binds to insulin-like growth factor 1 receptor (IGF1R).

17. The process of claim 1, wherein the maytansinoid comprises a thiol group.

18. The process of claim 17, wherein the maytansinoid is $N^{2'}$-deacetyl-$N^{2'}$-(3-mercapto-1-oxopropyl)-maytansine (DM1).

19. The process of claim 17, wherein the maytansinoid is $N^{2'}$-deacetyl-$N^{2'}$-(4-methyl-4-mercapto-1-oxopentyl)-maytansine (DM4).

20. The process of claim 1, wherein the antibody is chemically coupled to the maytansinoid via chemical bonds selected from the group consisting of disulfide bonds, acid labile bonds, photolabile bonds, peptidase labile bonds, thioether bonds, and esterase labile bonds.

21. The process of claim 1, wherein the bifunctional crosslinking reagent comprises an N-succinimidyl ester moiety, an N-sulfosuccinimidyl ester moiety, a maleimido-based moiety, or a haloacetyl-based moiety.

22. The process of claim 21, wherein the bifunctional crosslinking reagent is selected from the group consisting of N-succinimidyl 3-(2-pyridyldithio)propionate (SPDP), N-succinimidyl 4-(2-pyridyldithio)pentanoate (SPP), N-succinimidyl 4-(2-pyridyldithio)butanoate (SPDB), N-succinimidyl-4-(2-pyridyldithio)2-sulfo butanoate (sulfo-SPDB), N-succinimidyl 4-(maleimidomethyl)cyclohexanecarboxylate (SMCC), PEG-mal, sulfo-Mal, and CX1-1.

23. The process of claim 1, wherein the solution in step (a) comprises sucrose.

24. The process of claim 1, wherein the solution in step (a) comprises a buffering agent selected from the group consisting of a citrate buffer, an acetate buffer, a succinate buffer, and a phosphate buffer.

25. The process of claim 1, wherein the solution in step (a) comprises a buffering agent selected from the group consisting of HEPPSO (N-(2-hydroxyethyl)piperazine-N'-(2-hydroxypropanesulfonic acid)), POPSO (piperazine-1,4-bis-(2-hydroxy-propane-sulfonic acid) dehydrate), HEPES (4-(2-hydroxyethyl)piperazine-1-ethanesulfonic acid), HEPPS (EPPS) (4-(2-hydroxyethyl)piperazine-1-propanesulfonic acid), TES (N-[tris(hydroxymethyl)methyl]-2-aminoethanesulfonic acid), and a combination thereof.

* * * * *